(12) United States Patent
Goldstein

(10) Patent No.: US 7,191,183 B1
(45) Date of Patent: Mar. 13, 2007

(54) ANALYTICS AND DATA WAREHOUSING INFRASTRUCTURE AND SERVICES

(75) Inventor: Richard H. Goldstein, Cornwallville, NY (US)

(73) Assignee: RGI Informatics, LLC, Cornwallville, NY (US)

( * ) Notice: Subject to any disclaimer, the term of this patent is extended or adjusted under 35 U.S.C. 154(b) by 424 days.

(21) Appl. No.: 10/118,219

(22) Filed: Apr. 5, 2002

Related U.S. Application Data

(60) Provisional application No. 60/282,958, filed on Apr. 10, 2001.

(51) Int. Cl.
*G06F 17/30* (2006.01)

(52) U.S. Cl. .............................. 707/101; 707/6; 707/10; 707/100; 705/2

(58) Field of Classification Search .................... 707/6, 707/10, 100, 101; 705/2
See application file for complete search history.

(56) References Cited

U.S. PATENT DOCUMENTS

| | | | |
|---|---|---|---|
| 6,189,004 B1 * | 2/2001 | Rassen et al. .................. | 707/3 |
| 6,611,829 B1 * | 8/2003 | Tate et al. ...................... | 707/2 |
| 2002/0035562 A1 * | 3/2002 | Roller et al. ................... | 707/6 |

OTHER PUBLICATIONS

Saharia et al., "Enhancing data warehouse performance through query caching", ACM SIGMIS Database vol. 31, Issue 3 Summer 2000, pp. 43-63.*

Rogerson et al., "Automated Creation of Datamarts from a Clinical Warehouse, Driven by an Active Metadata Repository", American Medical Informatics Association Annual Symposium , Nov. 1998, pp. 1-2.*
"Sybase and RGI Informatics announce healthcare business intelligence solution focusing on quality improvement and medical error reduction," Sybase web pages, Apr. 10, 2000.
"Action Items: Sybase and RGI Announce Healthcare BI Solution" DSstar web pages, Apr. 18, 2000, vol. 4, No. 16.
w3Health web pages, www.w3health.com, printed Apr. 9, 2001.
Electronic Data Systems (EDS) web pages, www.aiimguide.com, printed Apr. 10, 2001.
CareScience web pages, www.carescience.com, printed Apr. 7, 2001.

(Continued)

*Primary Examiner*—Khanh B. Pham
(74) *Attorney, Agent, or Firm*—Law Office of Karen Dana Oster, LLC

(57) ABSTRACT

An analytics and data warehousing infrastructure and services system that uses an analytic rather than a transactional data model. The system preferably has at least one extracted source data store, at least one staging data store, and at least one analytic data store. The at least one staging data store preferably has at least one staging data table. The at least one analytic data store preferably has at least one analytic data table for storing transformed data. A staging data table loading algorithm may be used for populating the at least one staging data table with source data. A data transformation algorithm may be used for moving and transforming data from a staging data table into an analytic data store. Other algorithms that may be used in the present invention include algorithms for creating derived variables, creating event proxies, and restructuring data. In one preferred embodiment, the system is a data model based on a clinical rather than a financial understanding of healthcare.

31 Claims, 17 Drawing Sheets

OTHER PUBLICATIONS

Ingenix web page, www.ingenix.com, printed Apr. 9, 2001.
WebMD web pages, www.webmd.com, printed Apr. 7 and 10, 2001.
The Medstat Group web pages, www.medstat.com, printed Apr. 7, 2001.
TriZetto web pages, www.trizetto.com , printed Apr. 7, 2001.
IMS Health Canada web pages, www.imshealthcanada.com, printed Apr. 7, 2001.
Screaming Media, Business Wire, Java Industry Connection web pages, Insightful Announces S-Plus Analytic Server for Deployment of Java-Based Data Analytics; New UNIX Data Analysis Software Improves and Accelerates Decision-Making, http://industry.java.sun.com, Feb. 14, 2001 and printed Apr. 7, 2001.
Strategy Analytics web page, www.strategyanalytics.com, printed Apr. 7, 2001.
Creative Analytics, Inc. web page, www.creativeanalytics.com, printed Apr. 7, 2001.
NetMap analytics, web page, www.altaannalytics.com, printed Apr. 7, 2001.
IMS Health web pages, www.imshealth.com, printed Nov. 16, 2000.
IMS Health News, "IMS Health and Trizetto Terminate Merger Agreement," May 16, 2000 (from internet).
intelliClaim web pages, www.intelliclaim.com, printed Apr. 10, 2001.

* cited by examiner

ANALYTICS AND DATA WAREHOUSING INFRASTRUCTURE AND SERVICES

The present application is based on and claims priority from Provisional Patent Application Ser. No. 60/282,958, filed Apr. 10, 2001.

BACKGROUND OF THE INVENTION

The present invention is directed to advanced analytics, data mining, and data warehousing infrastructure and services and specifically to advanced analytics, data mining, and data warehousing infrastructure and services for the healthcare industry.

The National Academy of Sciences recently reported that in the United States as many as 98,000 people die each year from medical errors. The Academy's report estimated that the total cost of preventable mistakes—not only those that lead to death, but also those that incur medical disability expenses and lost productivity—could be as high as $29 billion a year. Healthcare providers understandably would like to find solutions to these medical errors.

Analytics provides business with a tool for finding solutions to problems. Analytics can be defined variously as the science of logical analysis, the branch of logic that deals with the process of analyzing, a method of logical analysis, or the application of computer and statistical techniques to the management of information. Advanced analytics is a process of finding and interpreting patterns from data. Advanced analytics (also called data mining) is a method of helping users extract useful information from large databases. It has been used in many industries for many years to provide information that can identify opportunities, predict outcome, and reduce risk. Software such as SAS's statistic and data management products, Silicon Graphics, Inc.'s (SGI) MineSet™, Insightful Corporation's S-PLUS Analytic Server™, and business intelligence application programs, such as Cognos Incorporated's COGNOS® or Brio Technology's BRIO® provide standard platforms for the development and delivery of analytical methods. Through these analytical methods or platforms quantitative information such as financial forecasts, research and development results, business performance, transaction information, and customer behavior and prediction can be analyzed and distributed.

Healthcare involves approximately 30 billion transactions yearly. Of these, more than 3 billion are electronic. The availability of electronic healthcare data has prompted a number of warehousing initiatives (data stores). These data stores contain a wealth of detailed information useful for clinical care, research, and administration. In their raw form, however, the data are difficult to use—there is too much volume, too much detail, missing values, inaccuracies, and a diversity of database architectures. As a result, conventional healthcare data warehousing solutions relate primarily to (1) the storage and preservation of data, and (2) providing answers to known questions, either through standard reports, structured ad hoc queries (parameter driven reports), or Standard Query Language (SQL) generators that require pre-programming to modify the architecture and metadata to allow for new queries or data types.

Several companies have begun to provide healthcare analytic and warehousing services to the healthcare industry. Examples of such companies include IMS Health, Inc., Solucient (previously HCIA, Inc.), and The MEDSTAT Group, Inc. IMS Health, Inc. is a developer of healthcare information solutions and market research for the pharmaceutical sector. Solucient is a provider of financial and medical benchmark information to healthcare providers, insurance companies, and pharmaceutical companies. The MEDSTAT Group, Inc. is a healthcare information database developer and provider of healthcare "analytics."

The analytic efforts of these companies have significant limitations. These limitations are due, in part, to their failure to successfully address a number of factors including: Health information is diverse, complex, and is not homogeneous; the architecture and composition of the analytic data stores are critical to the successful application of data mining tools; the analyst requires the ability to interactively refine the analytic model as part of the analytic process.

One example of a limitation of the known analytic efforts is that the analytic efforts of many of these companies utilize a highly structured data model and "business rules" which they incorporate in the model. The requirement for a well-defined model, governed by a set of pre-determined rules, is not suitable to data mining or knowledge discovery where the rules are yet to be discovered. For example, in order to add new elements or process new questions the model and the business rules must first be modified. Another example of a limitation of the known analytic efforts is that queries must be custom programmed or they require parameter driven or structured ad hoc queries that require a pre-defined role in the data model. Another exemplary limitation of the known analytic efforts is their need for a well-defined and limited domain such as pharmaceutical related data, UB92-hospital discharge abstracts, or insurance healthcare claims. In other words, they are not able to integrate or work across the many different data domains of healthcare. To perform advanced analysis, an analyst must be able to directly manipulate the analytic data tables, and refine these manipulations through iterative analysis. These limitations leave the known analytic efforts poorly suited for the analysis of clinical information outside of highly structured and limited domains. As a result, these analytic and warehousing services primarily answer known questions or sets of questions or simply respond to user requests for information such as reports or analysis.

Despite their claims, most of these companies focus on resource utilization and other non-clinical business aspects of healthcare. In other words, they employ financial rather than clinical data models. When they do provide clinical information it either is an expensive and time-consuming custom effort that provides a solution to answering a very specific question rather than a broad class of questions or relies on a limited list of published outcomes, such as those of the National Committee on Quality Assurance (NCQA) HEDIS® measures.

The W3Health Distributed Reporting System (DRS) network performance management module and the recently released DRS clinical performance management module are examples of analytic consulting systems. W3Health Corporation (W3Health) custom-builds this system for each healthcare organization customer. The system is primarily directed to managing risk and solving cost and utilization problems. It claims to use collected data to make better, faster decisions and gain a deeper insight into improving the quality of care. It is also available over the Internet, using an application service provider (ASP) model. The customized nature of the product makes it very expensive to implement. The system is further limited in that it requires clinical questions to be defined in advance. Further, the clinical performance management module bases much of its analysis against evidence-based medicine guidelines, DxCG, Inc.'s Diagnostic Cost Group (DCG) risk-adjustment models, HEDIS® effectiveness of care measures, and Evidenced Based Medicine (EBM) guidelines—not as a comparison to real data. Finally, W3Health's contemplated users are limited to healthcare payer and provider organizations.

The Internet is already having a significant impact on how the healthcare industry makes information available and how it processes transactions. Consumers are demanding access to Web-based healthcare information. Healthcare-related Web sites provide access to text-based information from numerous and growing electronic medical libraries. Healthcare providers are increasingly using the Internet as a means to access patient-based information, verify healthcare insurance eligibility, and process claims.

Driven in part by the Internet, the information requirements of the healthcare industry are rapidly changing. At all levels—provider, purchaser, and consumer—there is an increasing expectation that data (fact)-based information will help to improve quality, reduce cost, and support consumer choice. Most healthcare information technology environments, however, are focused primarily on supporting transactional rather than analytic systems. Recognizing the cost and complexity of creating and supporting an analytic environment, many healthcare organizations are looking for viable alternatives to buying, building, and maintaining their own analytic environment.

Companies or alliances of companies that bring their electronic commerce in healthcare transactions to the Internet include MedUnite, Inc. (MedUnite), Claimsnet.com (Claimsnet), The TriZetto® Group, Inc. (TriZetto), IMS Health, Inc. (IMS), Franklin Health, Inc. (Franklin Health), IntelliClaim, Inc. (IntelliClaim), and WebMD Corporation (WebMD). MedUnite is a consortium of major HMOs including Aetna, Inc., Oxford Health Plans, Inc., CIGNA, WellPoint Health Networks, Inc., and PacifiCare. ClaimsNet focuses on "on-line management of the $600 billion employer-based health benefit market." IMS Health focuses on the pharmaceutical industry. Franklin Health is supported by the national alliance of Blue Cross/Blue Shield organizations. IntelliClaim is a technology-based service that provides ASP plug-in solutions for their clients' claims-performance problems. WebMD® uses the power of the Internet to serve all aspects of the healthcare industry, from consumers to medical professionals.

BRIEF SUMMARY OF THE INVENTION

Health information data stores contain a wealth of detailed information useful for clinical care, research, and administration. In their raw form, however, the data are difficult to use—there is too much volume, too much detail, missing values, inaccuracies, and a diversity of database architectures.

To overcome these difficulties and to effectively respond to the industry drivers of cost and quality, the healthcare industry needs real effective advanced analytic solutions that include the clinical domain. To be effective, the solution must be flexible enough to take advantage of the fact that in analyzing clinical data, new knowledge is most often discovered by finding new questions, adding new data elements (without having to first modify the data model), and working freely across domains limited only by the availability of data.

The Healthcare Analytics Platform (the "HAP") of the present invention enables users to ask clinical questions of electronic data stores without knowing the questions in advance or without being limited to pre-defined questions. In other words, in addition to parameter-driven or structured ad hoc queries, the user is preferably able to independently author ad hoc queries. Futher, the present invention provides an information technology solution to the clinical analysis of healthcare data, and specifically addresses issues related to clinical quality, medical errors, healthcare costs, and differentiating quality. The present invention also supports a wide range of clinical and epidemiological research endeavors. This then provides the user of the present invention with a fact (evidence-based) system to discover new knowledge, test clinical hypotheses, determine quality, reduce risk, and improve patient care. This allows the user to extract value from data stores by providing an easily accessible and accurate means by which consumers, purchasers, and providers of healthcare can differentiate and evaluate the quality of healthcare providers and plans.

The present invention encompasses a set of analytic and data warehousing tools and services that incorporate proprietary analytic structures and algorithms. The present invention is a business intelligence solution tailored to the clinical domain. Specifically, the present invention consists of a data model that (1) is designed to support analytic rather than transactional activities, (2) is based on a clinical rather than a financial understanding of healthcare and the properties of healthcare data, and (3) provides algorithms for the user to independently author ad hoc queries. The nature of the clinical model, resultant data structures, and algorithms allow for the present invention application across a wide variety of healthcare data with a minimal amount of customization beyond the basic extract, transform, and load (ETL) process.

In one preferred embodiment the present invention is implemented, at least in part, as an ASP and/or Internet delivery model (an "ASP/Internet delivery model").

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 1:
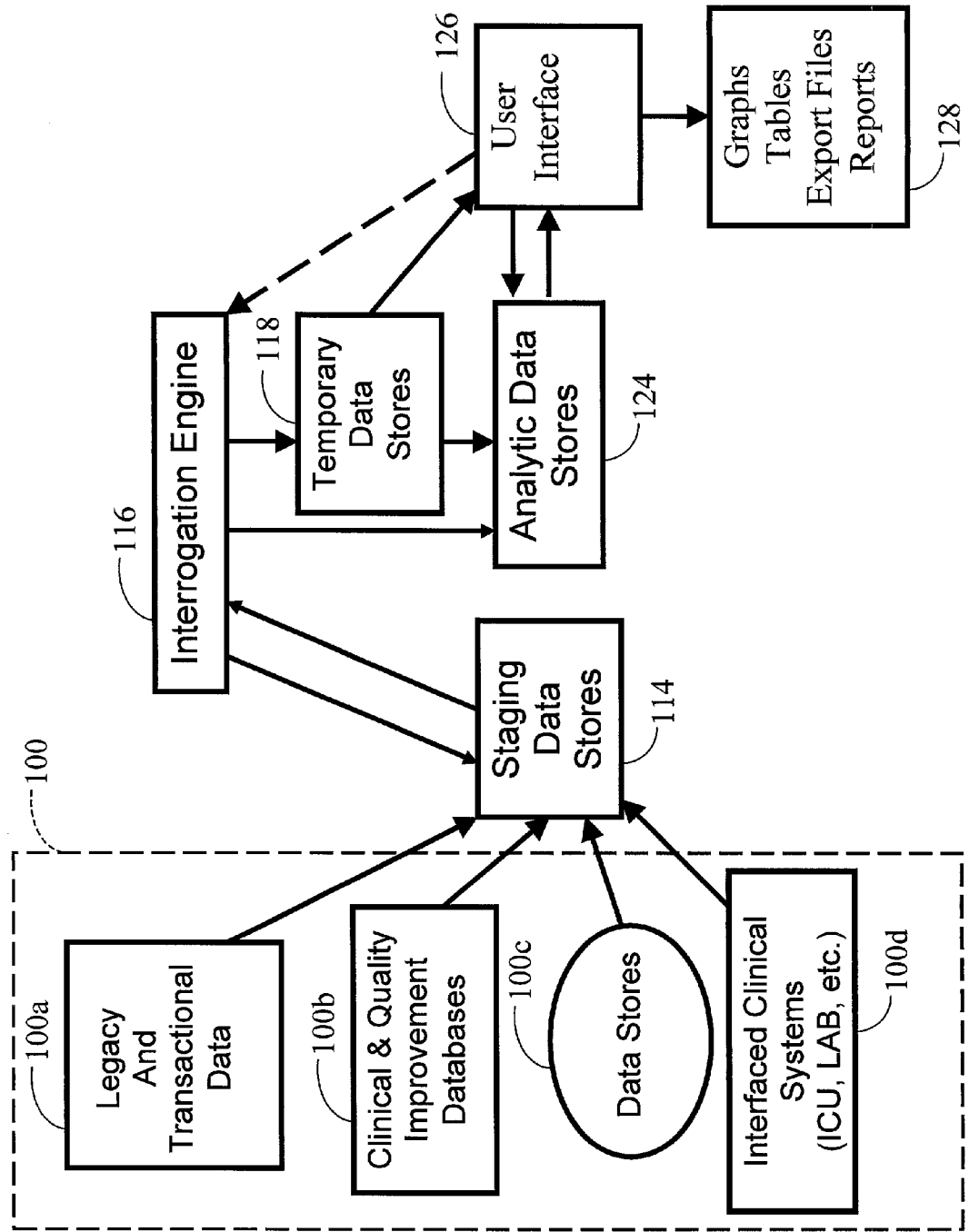
FIG. 1 is a schematic diagram of an exemplary preferred embodiment of the system of the present invention.

The present invention is directed to analytic and data warehousing infrastructure and services (FIGS. 1 and 2) that provide a way to extract value from clinical or source data stores 100 (which includes, for example, legacy and transactional data 100*a*, clinical and quality improvement databases 100*b*, general data stores 100*c*, interfaced clinical systems 100*d*, and specific healthcare data stores 136 (FIG. 2)). The present invention specifically addresses issues related to clinical quality, medical errors, healthcare costs, and differentiating quality and supports a wide range of clinical and epidemiological research endeavors. This then provides the user of the present invention with a fact (evidence) based system to discover new knowledge, test clinical hypotheses, determine quality, reduce risk, and improve patient care.

For purposes of this disclosure, the term "data stores" is used to describe stored information. For clarity, the data stores used by the invention have been divided into four separate categories of tables: source data stores 100, staging data stores 114, temporary data stores 118, and analytic data stores 124. Source data stores 100 have been defined above and exemplary source data tables are set forth below as "Source Data 1: ED Source Data File" and "Source Data 2: Procedure Flat File Extract." As is also set forth above, the present invention extracts and loads the source data from the source data stores 100 into staging data tables 114 of the staging data stores. The staging data tables 114, which are relational data stores in a uniform database environment, are then used by the interrogation engine 116. Exemplary individual tables found in the staging data stores 114 might include "Staging Data Table 1: Hospital Encounters" and "Staging Data Table 2: Procedures." As set forth above, the interrogation engine 116 interrogates the staging data tables 114, creating new variables from the source data and restructuring the data for analysis as an analytic data store 124. More specifically, the interrogation engine 116 provides for the partial denormalization (summarization) of staging data tables 114 to the modified star schema (dimensional) organization of the present invention's analytic data stores 124. Exemplary individual analytic data tables found in the analytic data stores 124 include "Analytic Data Table 1: Hospital Encounters," "Analytic Data Table 2: ED Table," "Analytic Data Table 3: Procedures," "Analytic Data Table 4: Cardiology," "Analytic Data Table 5: User Results, ccabg," "Analytic Data Table 6: Abrupt Vessel Closure," "Analytic Data Table 7: Critical Care Detail," and "Analytic Data Table 8: Tachycardia." The analytic data tables are filled with analytic data elements. Temporary data stores 118 are used to store temporary data tables that are created during the creation of analytic data stores 124 as well as in the analytic process. Exemplary individual temporary data tables found in the temporary data stores 118 may include "Temporary Data Table 1: Hospital Encounters," "Temporary Data Table 2: Hospitalization After a Return to ER," "Temporary Data Table 3: Cardiovascular Procedures," "Temporary Data Table 4: Cardiovascular Procedures By Day," "Temporary Data Table 5: Cardiovascular Procedure Physician Identifiers," "Temporary Data Table 6: Cardiovascular Procedures By Hospitalization."

FIG. 1 shows an exemplary embodiment of the present invention. As shown, input into the system may come from any type of clinical or source data stores 100. Clinical or source data stores 100 might include, for example, legacy and transactional data and systems 100*a*, clinical and quality improvement databases 100*b*, data stores 100*c*, and/or interfaces clinical systems 100*d* (collectively referred to as "source data stores 100"). Information or source data from these source data stores 100 is extracted for use in the HAP 110. The present invention extracts and loads the source data into staging data tables 114 which are then used by the interrogation engine 116. The interrogation engine 116 interrogates the staging data tables 114, creating new variables from the source data and restructuring the data for analysis. The product of the interrogation engine 116 is an analytic data store 124. A browser based graphical user interface 126 is used to create ad hoc reports, generate data exports (standard reports and/or libraries), or allow for interactive analysis 128.

Figure 2:
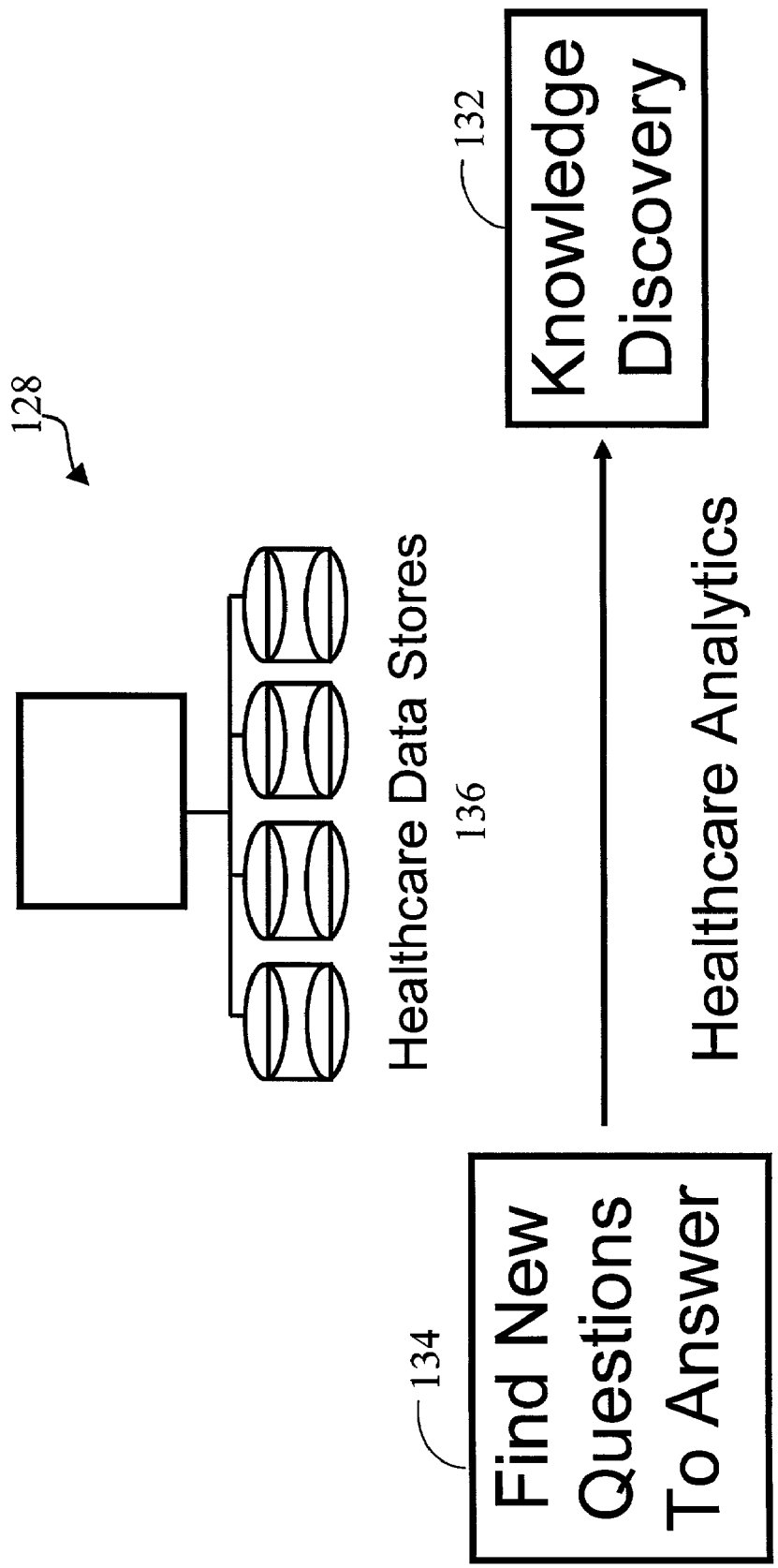
FIG. 2 is a high level schematic diagram of the functional characteristics of the system of the present invention.

As shown in FIG. 2, used correctly, the present invention can use advanced analytic techniques 130 to discover new knowledge (knowledge discovery 132) by finding new questions to answer 134 (also referred to as clinical questions or ad hoc queries), not just find the answers to known questions (decision support). The present invention also provides for a fact (evidence) based methodology to validate expert opinions, especially as incorporated in clinical guidelines or protocols. Specifically, the present invention enables users to ask clinical questions 134 of health information data stores 136 without knowing the questions in advance (independent authoring of ad hoc queries 134). In other words, instead of parameter-driven structured ad hoc queries, the user is preferably able to independently author ad hoc queries 134. The response time for these questions in the analytic environment of the present invention is preferably rapid (seconds/minutes). The present invention uses proprietary analytic structures and algorithms to create advanced analytic solutions specifically tailored to the clinical domain of healthcare. In other words, advanced analytics may be extended to the clinical domain to differentiate and improve clinical quality.

Users

Users of the present invention may include one or more of the following exemplary types of individuals or organizations: healthcare providers, fiscal intermediaries, purchasers of healthcare, providers of healthcare analytics, and individual consumers. Healthcare providers may include, for example, hospitals 140, physicians 141, pharmaceuticals, and other healthcare provider individuals or organizations. These healthcare providers may be interested in comparing quality and cost with their competitors as well as improving the quality of care they deliver. Fiscal intermediaries or payers may include insurance companies and HMOs. These fiscal intermediaries may be interested in monitoring healthcare providers, differentiating quality, and controlling medical loss. Purchasers of healthcare may include large employers, state governments, and federal governments. These purchasers of healthcare may be interested in determining the best value (most cost-effective) for their employees that would also be profitable to them. Providers of healthcare analytics and information may include healthcare e-portals and analytic shops. These providers of healthcare analytics might use the present invention as a primary portion of their services or as a comparison to their own conclusions. This could be done by allowing access to the invention to provide access to databased healthcare information. Finally, individual consumers (patients) may be interested in using the present invention as a means for searching for both quality and value in healthcare providers or plans.

Figure 3:
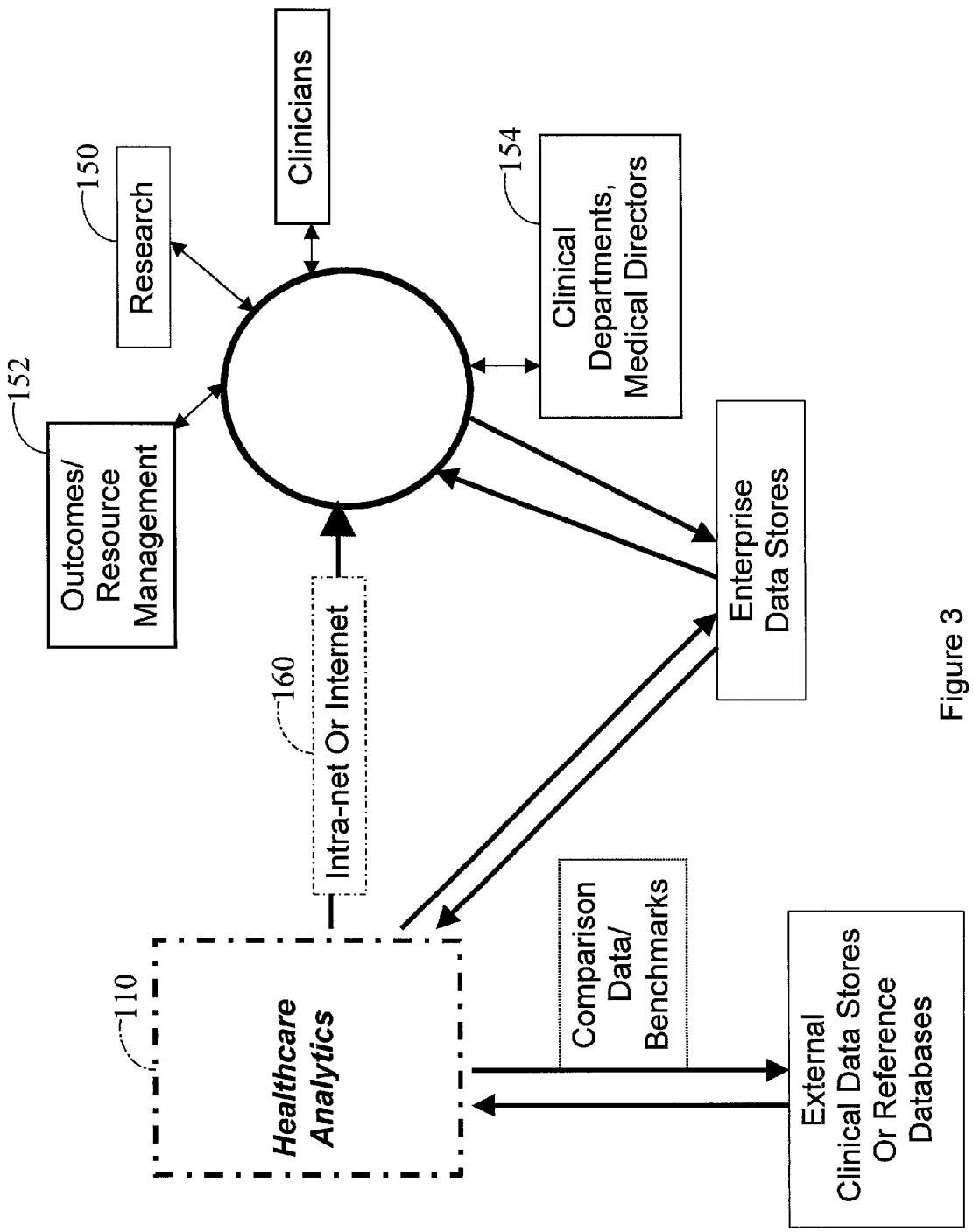
FIG. 3 is a schematic diagram of an exemplary preferred embodiment of the system of the present invention showing user access and flow of information out of the system.
Figure 4:
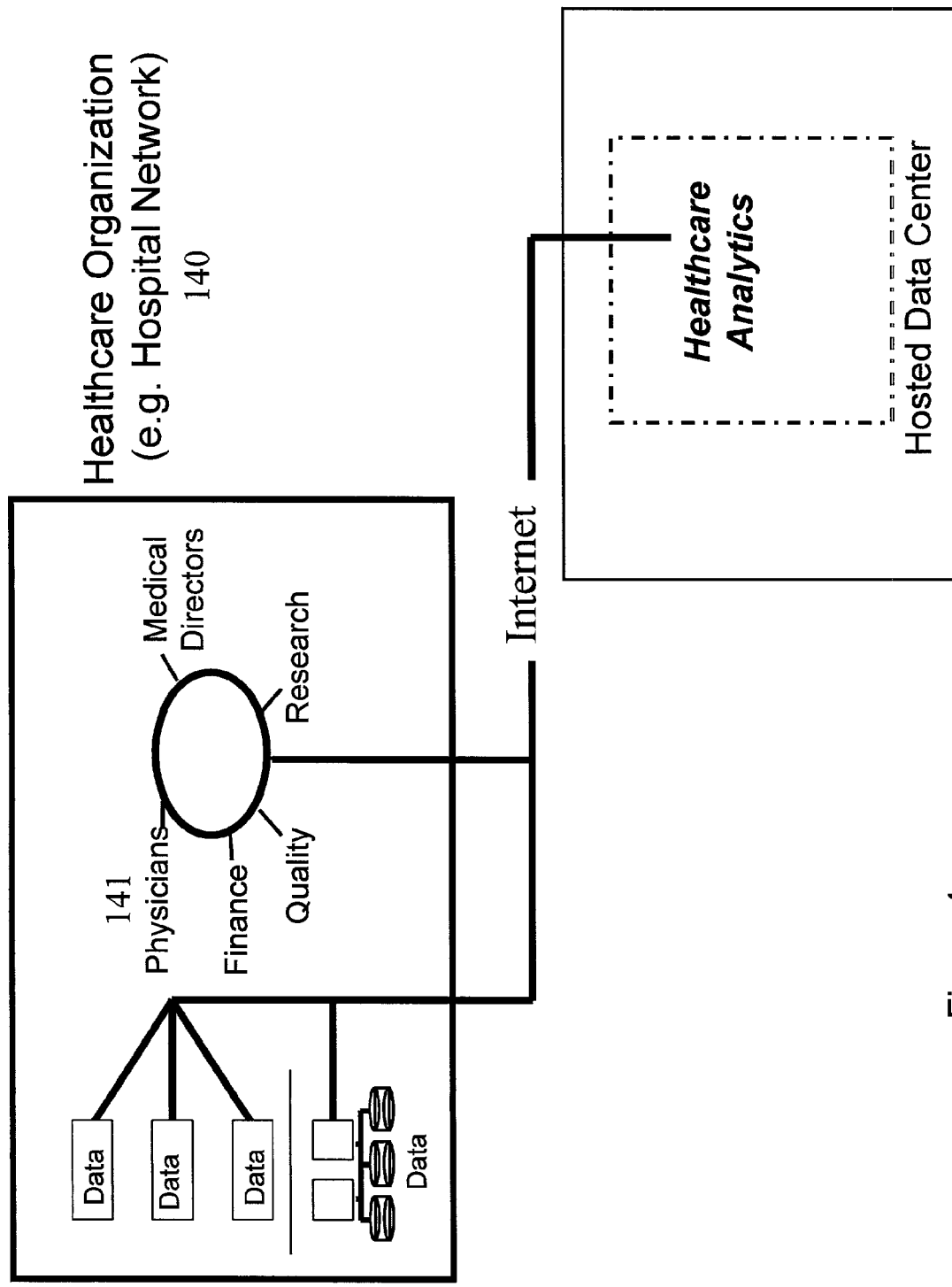
FIG. 4 is a schematic diagram of an exemplary preferred embodiment of the system of the present invention implemented as an ASP/Internet delivery model and connected through an Internet Service Provider or data center to users.

As shown in the exemplary embodiments of FIGS. 3 and 4, multiple types of users may use the present invention simultaneously. The users may have non-uniform systems located anywhere. The users may use the present invention in any number of ways, including but not limited to research 150, outcome/resource management 152, case management, disease management, operations, marketing, actuaries, and clinical and epidemiological research 154. The users may be connected to the present invention using any known connection means, including but not limited to Internet 160, intranet 160, hard wiring, dial-up, online analytical processing (OLAP) tools 162, and application program interfaces (API). The present invention can also export data to other data mining, visualization or statistical software applications, external reference or accredating bodies, or enterprise data stores if the user so desires.

Source Data

Healthcare organizations generate source data in many different ways, often with different systems. To accommodate a variety of source data store 100 environments (e.g. ORACLE®, SAS Institute Inc.'s SAS™, SYBASE Inc.'s SYBASE®, IBM Corporation's DB2®, Microsoft Corporation's MICROSOFT ACCESS®, and Microsoft Corporation's MICROSOFT EXCEL™), the present invention can preferably extract or receive data from any source data store 100 that is compliant with open database connectivity (ODBC) standards which is an industry-standard interface that makes it possible to access different database systems with a common language, SQL compliant data stores, or any application capable of producing flat files. (The present invention could be modified to extract or receive data from other types of source data stores 100.) Finally, the present invention preferably extracts source data using commercially available software tools, or it can map from flat files. An example of this, Source Data 1: ED Source Data File (discussed in relation to Example 1), shows source data exported by the transactional clinical information system of a healthcare organization, and extracted as a fixed format flat file. The present invention uses the source data extracted from the data provided by healthcare organizations to populate a staging data table. Source Data 1: ED Source Data File shows two lines of observations in a flat file and Staging Data Table 1: Hospital Encounters shows variables that define the data that should be found in the source data. In other words, it would be expected that each variable in the staging data table would have an associated value in the respective line of source data. Using Algorithm 1, an exemplary algorithm used to populate the staging data tables, each variable is assigned its respective value. The results are Observation 1 and Observation 2. Values that are not found are indicated by a "." symbol. A true staging data table could be comprised of any number of observations.

Interrogation Engine

Figure 5:
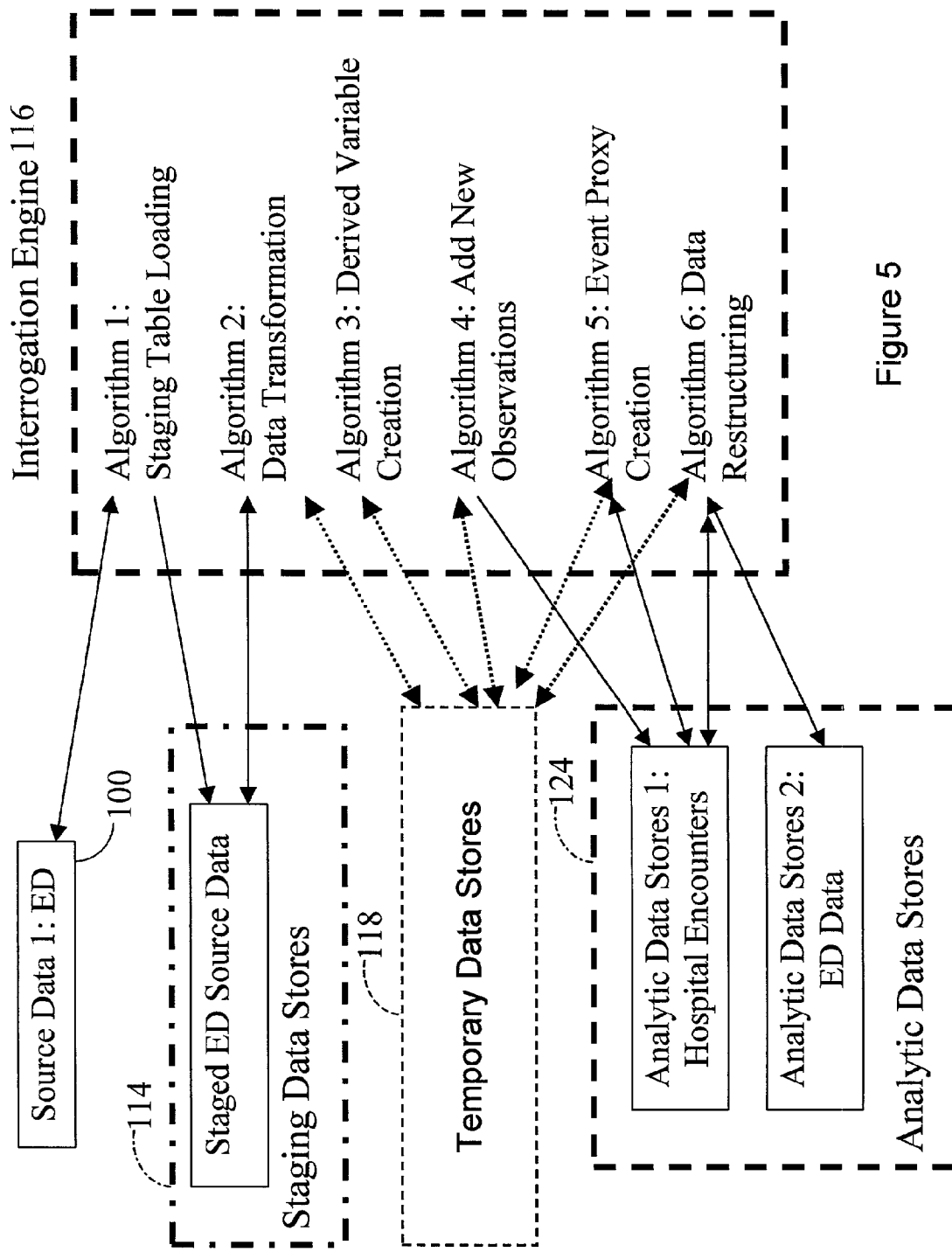
FIG. 5 is a schematic diagram of an exemplary preferred embodiment of the process flow of the interrogation engine used in Example 1.

The interrogation engine 116 of the present invention transforms data, creates new variables from the source data stores 100 and stores them in the staging data tables, and then restructures the data making it both ready and available for analysis as analytic data stores 124. Through these processes, the interrogation engine 116 provides for the partial denormalization (summarization) of staging data tables 114 to the modified star schema (dimensional) organization of the present invention's analytic data stores 124; incorporating an understanding of the clinical as well as the operational domain of healthcare. It should be noted that any combination of interrogations might be used. It should be further noted that the interrogations shown and described are exemplary and are not meant to limit the scope of the invention. FIG. 5 shows an exemplary embodiment of an interrogation engine 116 of the present invention interrogating (using Example 1, Algorithms 2–6) the staged data (staging data tables) and creating analytic data tables (for example, Analytic Data Table 1: Hospital Encounters Observation 1 and Analytic Data Table Observation 2).

Exemplary interrogations of the present invention provide for the derivation of new data elements from the staged data. For example, inpatient mortality is a new data element that can be derived from standardized hospital data sets (e.g. UB92) discharge dispositions. To do this, Algorithm 3 may be used to create derived variables such as event proxies for death, discharge against medical advice, and age at time of admission. Using a data store of UB92 dispositions and the event proxy for death, the new data element for inpatient mortality can be derived.

Another example of a derived variable is an "event proxy." Here the interrogation engine 116 of the present invention creates a new (derived) variable from staging data table data that identifies a specific clinical occurrence (event). Clinical examples might include an emergency CABG after coronary artery angioplasty as a proxy for abrupt vessel occlusion; a peri-operative ischemic event as a proxy for the pre-operative assessment of the patient; a rate of hospitalization or emergency room (ER) visits by asthma patients as a proxy for quality of management of care; and a hold placed after voluntary admission to a psychiatry unit as a proxy for the quality of the initial physician assessment.

Advanced analysis generally uses mathematical denominator values that reflect the question or unit of analysis. For example in examining in-patient mortality rates (morality rate=[occurrences/sample size]*1/100), the numerator is the number of patients who died while hospitalized (discharge disposition is died) and the denominator must represent the number of hospital discharges for the study period—not the number of procedures or lab tests of patients hospitalized during that time interval. To create analytic data tables 124 that reflect the appropriate unit of analysis (denominator), the present invention's interrogation engine 116 restructures (denormalizes) the staged data. An example of this process is summarization. Source data stores 100 may have one blood potassium reading for one patient and ten for another. The mean potassium from these tables reflects the mean of lab tests, not patients. The interrogation engine 116 of the present invention creates an analytic data table that provides a denominator directly relating to the clinical unit of inquiry—i.e. what is the mean potassium of postoperative critical care patients; or for each patient what was the maximum or minimum blood potassium reading.

The present invention's interrogation engine 116 also filters the data to remove background noise. For example, a data set for asthma patients derived from claims data may initially have a million rows. Many of these rows contain mostly background noise that, although vital in a financial model, impair clinical analysis. The present invention would transform this million-row data set into one containing about ¼ of the rows (250,000). Specifically, rather than simply pivoting the data from rows to columns, the present invention makes specific use of the behavior of healthcare data to differentiate noise from useful data. For example, the cost data present in each of the rows may be useful data, but some diagnostic information is not very useful. For example, diagnostic information associated with the venupuncture procedure is generally less accurate than that associated with a physician performed or hospital based procedure, but venupuncture procedure infarction occurs frequently in a claims based data warehouse. The diagnostic information associated with the venupuncture procedure creates "noise" during the analysis of diagnosis codes in claims derived source data stores 100 both by distorting the frequency of the occurrences of some diagnoses and, by a variation in coding, accuracy. In this example, by eliminating diagnosis associated with venupuncture, the present invention could reduce the size of one analytic data table from one million to 300,000 rows; eliminating 700,000 rows of "background noise." Dropping all diagnostic information associated with venupuncture, and summarizing the cost information is one example of how the present invention converts multi-million row/gigabyte sized data sets to those of hundreds of thousands of rows and megabytes and, more importantly, eliminates the background noise.

The staging data tables 114, interrogation engine 116, and analytic data stores 124 can accommodate most new data elements without first changing the data model. The architecture of the present invention utilizes a modified "entity—attribute—value (EAV)" schema. In an EAV schema, the "entity" columns identity the patient, date, and time of the variable, the "attribute" identifies what the variable represents (i.e. heart rate, discharge disposition, serum potassium), and the "value" represents the stored result. Most analytic data models are highly dependent on business rules, and usually require the pre-programming of new elements. This pre-programming is often time consuming and costly. The present invention preferably requires that to use new data elements, a user (not the data model) have domain (clinical) knowledge, i.e. what a venupuncture procedure means. This allows the present invention to accept new data without first modifying the model. As the user gains knowledge regarding the new data element through the analytic process, the model can be modified to reflect the insights gained by the accumulated knowledge.

The action of the interrogation engine 116 and the design of the analytic data stores 124 combine to provide for a robust and flexible analytic architecture which allows analysis to be based on events, occurrences over time (time series) stratification within thse analyses, and ad hoc independent user definition of events and stratafications. Here, the interrogation engine 116 has a second role in providing for ad hoc analysis and data mining, allowing the user to create new user defined (custom) analytic events, and stratifications. An event can represent, for example, a death, a procedure, a consultation, a hospital admission, an intensive care unit stay, an episode of tachycardia, or hypokalemia. In analyzing clinical data, the present invention defines events by elements in the analytic data stores 124 (or alternatively the staging data tables 114). Most events have an associated time and date. Many have associated values. For example, an episode of tachycardia may have an associated mean or maximum heart rate value. Simple events or combinations of events may be used to define more complex events. Intubation, ventilation, weaning, and extubation are events that define mechanical ventilation. The same event can be used to define a clinical manifestation, an outcome, or an intervention 110 depending on the analytic context. The present invention both provides a library of pre-defined events and assists the user in defining new events from elements in the analytic data stores 124. In the analysis of events, the present invention allows the user to analyze the event frequency, duration, and component values, as well as the relationship and time between events.

Example 1

FIG. 5 shows an exemplary process or flow of data in the interrogation engine 116. The algorithms set forth below are exemplary embodiments of the individual steps of the process. Specifically, the code (written in the STATA®'s programming language for the purpose of these examples, but not limited by programming language) illustrates how the present invention, loads extracted data into staging data tables and then interrogates the staging data tables to create analytic data stores 124. Example 1 is directed to data from an emergency department (ED). FIG. 5 shows the exemplary process used in Example 1.

In this example, extracted ED source data (Source Data 1: ED Source Data File) has a row for every time a patient uses the hospital's emergency department (ED).

Each row represents one ED visit. The resultant analytic data table (ED) will include for each ED visit a number of proxy events (e.g. a proxy event indicating a second ED visit within seven days of a prior visit (e7) or a proxy event indicating hospitalization within seven days of an ED visit (h7)). This code also illustrates how the present invention creates event proxies, denormalizes staging data stores 114 to the analytic data tables 124 at the level of the unit of analysis (ED visits+Hospitalizations=>ED visits), and captures the relationship, in time, of one event to another.

Source Data 1: ED Source Data File shows two lines of exemplary source data from an ED source data file. The source data is in flat file format. In this example, the dates and identifiers are corrupted. Specifically, a "." indicates a missing value.

Source Data 1: ED Source Data File

LXXXXXXX MXXXXX 'NameXXXXXXX    '12/31/78 01/01/79
M xxxx413 '883.0'EM RTN . . . 0380 '883.0' . . . 9   289.00
378.00  1 (end of row)
Lxxxxxxx MXX376 'NameXXXXXXXXXXE    '12/31/70 01/01/71
F xxxx430 '464.4'EM RTN . . . 038xxx0 '464.4'. . . 3   397.00
402.02    1 (end of row)

Once the source data is extracted to a flat file, using a staging table loading algoritm (such as Algorithm 1: Staging Table Loading the present invention loads the flat file into the uniform data store environment of the staging data tables 114 (for example, Staged ED Source Data 206 (e.g. Data Table 1: Hospital Encounters) of the Staging Data Stores 114. Algorithm 1 is an exemplary staging data table loading algorithm used to make this transition. The variable report1 found in the first line of the loading algorithm refers to the Hospital Encounter Dictionary that maps the ASCII characters of the Source Data 1: ED Source Data File flat file.

| Dictionary 1: Hospital Encounter Dictionary | | | |
|---|---|---|---|
| dictionary { | | | |
| _lrec1(178) | | | |
| _column(1) | str10 | ln | %10s |
| _column(12) | str8 | mr | %8s |
| _column(22) | str25 | name | %25s |
| _column(49) | str8 | adate | %8s |
| _column(58) | str8 | ddate | %8s |
| _column(67) | str1 | s | %1s |
| _column(69) | int | byr | %4f |
| _column(73) | int | bmo | %2f |
| _column(75) | int | bda | %2f |
| _column(79) | str5 | adx | %5s |
| _column(87) | str2 | p | %2s |
| _column(92) | str3 | d | %3s |
| _column(98) | str2 | mor | %2s |
| _column(100) | int | drg | %3f |
| _column(104) | str6 | md1 | %6s |
| _column(112) | str5 | pdx | %5s |
| _column(120) | double | proc1 | %5f |
| _column(126) | str8 | pdate | %8s |
| _column(135) | str6 | md2 | %6s |
| _column(142) | str3 | an | %3s |

-continued

| | | | |
|---|---|---|---|
| _column(150) | int | mdc | %2f |
| _column(153) | float | cost | %10f |
| _column(164) | float | chg | %10f |
| _column(176) | int | los | %3f |
| } | | | |

Algorithm 1: Staging Data Table Loading

```
infile using hospital_encounter.dct,using (Source Data 1)
    capture drop eddate
    capture drop
    capture drop month
        encode s,gen (sex) label(sexfmt)
        encode d,gen (disp) label(disp)
        encode p,gen (priority) label (priority)
        drop s p d
        gen encounter=ed
        save staging/hospital_encounters
```

The data from Source Data 1: ED Source Data File, the ED source flat file, is then staged in a relational staging data table with the following variables:

Staging Data Table 1:
Hospital Encounters (Variables)

| variable name | storage type | display format |
|---|---|---|
| ln | str10 | %10s |
| mr | str8 | %9s |
| name | str25 | %25s |
| adate | str8 | %9s |
| ddate | str8 | %9s |
| s | str1 | %9s |
| byr | int | %8.0g |
| bmo | int | %8.0g |
| bda | int | %8.0g |
| adx | str5 | %9s |
| p | str2 | %9s |
| d | str3 | %9s |
| mor | str2 | %9s |
| drg | int | %8.0g |
| md1 | str6 | %9s |
| pdx | str5 | %9s |
| proc1 | double | %10.0g |
| pdate | str8 | %9s |
| md2 | str6 | %9s |
| an | str3 | %9s |
| mdc | int | %8.0g |
| cost | float | %9.0g |
| chg | float | %9.0g |
| los | int | %8.0g |
| en | str8 | %8s |

The two lines from the flat file are now captured as observations in Staging Data Table 1: Hospital Encounters (Observations).

Staging Data Table 1: Hospital Encounters (Observations)

Observation 1:

| Ln | Lxxxxxxxx | mr | Mxxxxxxxx | name | xxxxxxxxxxx |
|---|---|---|---|---|---|
| adate | 12/31/78 | ddate | 01/01/79 | s | M |
| byr | 199x | bmo | 4 | bda | 13 |
| adx | 883.0 | p | EM | d | RTN |
| mor | . | drg | . | md1 | 038xx |
| pdx | 883.0 | proc1 | . | pdate | . |
| md2 | . | an | . | mdc | 9 |
| cost | 289 | chg | 378 | los | 1 |
| en | er | | | | |

Staging Data Table 1: Hospital Encounters (Observations)

Observation 2:

| Ln | Lxxxxxxxx | mr | Mxxxxxxxx | name | xxxxxxxxx |
|---|---|---|---|---|---|
| adate | 12/31/70 | ddate | 01/01/71 | s | F |
| byr | 19xx | bmo | 4 | bda | 30 |
| adx | 464.4 | p | EM | d | RTN |
| mor | . | drg | . | md1 | 038xx0 |
| pdx | 464.4 | proc1 | . | pdate | . |
| md2 | . | an | . | mdc | 3 |
| cost | 397 | chg | 402.02 | los | 1 |
| en | er | | | | |

As shown in FIG. 5, the interrogation engine 116 then interrogates the staging data tables in the staging data stores 114 to create the corresponding analytic data stores 124. The interrogation engine 116 applies a series of algorithms to the data in the staged observations, and joins the newly interrogated data to the appropriate analytic data table in the analytic data stores 124. Algorithms 2–4 illustrate the process of transforming the data (Algorithm 2), creating derived variables (Algorithm 3), and adding new observations (Algorithm 4).

Algorithm 2 is an exemplary data transformation alorithm that changes the data storage formats of the staging data tables to those suitable for analysis. Specifically, Algorithm 2 is used to transform the data from the staging data table 114 to analytic data stores 124 that can be used by the interrogation engine 116. For example, Algorithm 2 may be used to create elapsed time elements that can be substituted for string representations of date and time (string dates or string representations (e.g. "12/3/1983" or "Jul. 4, 2001")) in the data are converted to elapsed time elements (a number of days or other pre-defined time periods from a predetermined time). Algorithm 2 may also be used to change storage types and encode string representations to numeric values.

Algorithm 2: Data Transformation

```
use staging/hospital_encounter
gen eadate=date(adate,"mdy",2010) /*change string date to elapsed date*/
gen eddate=date(ddate,"mdy",2010) /*change string date to elapsed date*/
gen year=year(eadate) /*derrive year from elapsed admission date*/
drop adate ddate /*drop string dates from tables*/
gen double lid=real(substr(ln,2,9)) /*convert identifiers from numeric
to string*/
gen double mid=real(substr(mr,2,7)) /*convert identifiers from numeric
to string*/
gen phy=real(md1) /*convert identifiers from numeric to string*/
gen surg=real(md2) /*convert identifiers from numeric to string*/
drop md1 md2 /*drop numeric identifiers*/
drop if lid==. /* drop lines without an identifier*/
save temp/hosptial_encounters,replace
```

Algorithm 2: Data Transformation transforms the data, including adding the emphasized information to Staging Data Table 1: Hospital Encounters to create Temporary Data Table 1: Hospital Encounters.

Temporary Data Table 1:
Hospital Encounters (Observations)
Observation 1:

| ln | LXXXXXXXX | mr | MXXXXXX | name | XXXXXXXXX |
|---|---|---|---|---|---|
| adx | 883.0 | mor | . | drg | . |
| pdx | 883.0 | proc1 | . | pdate | . |
| an | . | | mdc | 9 | cost | 289 |

Temporary Data Table 1:
Hospital Encounters (Observations)
Observation 1:

| | | | | | |
|---|---|---|---|---|---|
| chg | 378 | los | 1 | sex | M |
| disp | RTN | priority | EM | en | ER |
| eadate | -xxx | eddate | -xxxx | year | 19xx |
| lid | xxxxxxxx | mid | xxxxxxxx | phy | 388x0 |
| surg | . | | | | |

Algorithm 3: Derived Variable Creation is an exemplary algorithm that creates derived variables such as event proxies for death, discharge against medical advice, and age at time of admission.

Algorithm 3: Derived Variable Creation

```
use temp/hostpial_encounters
    gen mort=1 if disp==2 /*mortality as categorical value based on variable disp==EXP*/
        replace mort=0 if disp~=2
        gen ama=1 if disp==1 /*discharge against medical advice catigorical from disp==AMA*/
        replace ama=0 if disp~=1
        gen ebdate=mdy(bmo,bda,byr)
        gen age=int((eadate-ebdate)/365)
        drop bmo bda byr
    sort lid
        quietly by lid:assert _N==1
    sort ln
save temp/hosptial_encounters,replace
```

Algorithm 3: Derived Variable Creation adds the emphasized derived data to Temporary Data Table 1: Hospital Encounters.

Temporary Data Table 1: Hospital Encounters (Observations)

Observation 1:

| | | | | | |
|---|---|---|---|---|---|
| ln | Lxxxxxxx | mr | Mxxxxxxx | name | xxxxxx |
| adx | 883.0 | mor | . | drg | . |
| pdx | 883.0 | proc1 | . | pdate | . |
| an | . | mdc | 9 | cost | 289 |
| chg | 378 | los | 1 | sex | M |
| disp | RTN | priority | EM | en | er |
| eadate | -2xxx | eddate | -1xxxx | year | 19xx |
| lid | xxxxxxxx | mid | xxxxxx | phy | 38xx0 |
| surg | . | mort | 0 | ama | 0 |
| ebdate | 1xxxx | age | 94 | | |

Algorithm 4: Adding New Observations may be used to add new observations to the existing Analytic Data Table 1: Hospital Encounters.

Algorithm 4: Adding New Observations
(Updating The Analytic Data Tables)

```
use analytic/hopsital_encounters /*this is the hospital encounter analytic data table, Analytic Data Table 1: Hospital Encounters*/
clear
sort ln
merge ln using temp/hopsital_encounters /*add the new observations*/
capture drop _merge
save analytic/hopsital_encounters,replace
```

The resulting Analytic Data Stores 1: Hospital Encounters has the variables and oberservations defined in Analytic Data Table 1: Hospital Encounters (Variables) and (Observations).

Analytic Data Table 1:
Hospital Encounters (Variables)

| variable name | storage type | display format |
|---|---|---|
| ln | str10 | %10s |
| mr | str8 | %9s |
| name | str25 | %25s |
| adx | str5 | %9s |
| mor | str1 | %9s |
| drg | int | %8.0g |
| pdx | str5 | %9s |
| proc1 | double | %10.0g |
| pdate | str8 | %9s |
| an | str3 | %9s |
| mdc | byte | %8.0g |
| cost | int | %9.0g |
| chg | float | %9.0g |
| los | byte | %8.0g |
| en | str8 | %8.0s |
| sex | byte | %8.0g |
| disp | byte | %8.0g |
| priority | byte | %8.0g |
| eadate | int | %9.0g |
| eddate | int | %9.0g |
| year | int | %9.0g |
| lid | long | %10.0g |
| mid | long | %10.0g |
| phy | float | %9.0g |
| surg | float | %9.0g |
| mort | byte | %9.0g |
| ama | byte | %9.0g |
| ebdate | int | %9.0g |
| age | byte | %9.0g |

Analytic Data Table 1: Hospital Encounters (Observations)

Observation 1:

| | | | | | |
|---|---|---|---|---|---|
| ln | Lxxxxxxx | mr | Mxxxxxxx | name | xxxxxx |
| adx | 883.0 | mor | . | drg | . |
| pdx | 883.0 | proc1 | . | pdate | . |
| an | . | mdc | 9 | cost | 289 |
| dig | 378 | los | 1 | sex | M |
| disp | RTN | priority | EM | en | er |
| eadate | -2xxx | eddate | -2xxxx | year | 19xx |
| lid | xxxxxxxx | mid | xxxxxx | phy | 38xx0 |
| surg | . | mort | 0 | ama | 0 |
| ebdate | 1xxxx | age | 94 | | |

Exemplary Algorithm 5 interrogates both hospital discharge and ED encounter data present in the hospital encounter analytic data tables. Specifically, the interrogation engine 116 uses algorithms to create event proxies for hospitalization within seven days of an ED visit (h7), a second ED visit within seven days of a prior ED visit (er7), and a hospitalization within seven days of a second ED visit (er7h7), and then save the proxy data in Temporary Data Table 2.

Interrogation engine 116 uses algorithms to create event proxies for hospitalization within seven days of an ED visit (h7), a second ED visit within seven days of a prior ED visit (er7), and a hospitalization within seven days of a second ED visit (er7h7).

Algorithm 5: Event Proxy Creation

```
use analytic/hospital_encounters /*this is the hospital encounter
analytic
           data table, Analytic Data Table 1: Hospital Encounters */
       quietly by mr:gen h7=1 if
           t[_n+1]=="hos"&eadate[_n+1]-eddate<=7&er==1
       quietly by mr:gen er7=1 if
           t[_n+1]=="er"&eadate[_n+1]-eddate<=7&er==1
       quietly by mr:gen er7h7=1 if er7==1&h7[_n+1]==1
   keep if er7h7==1|h7==1|er7==1
   keep ln e7h7 h7 er7
sort ln
save temp/e7h7
```

Algorithm 5: Event Proxy Creation then saves the event proxy data in a temporary data table (Temporary Data Table 2: Hospitalization After a Return to ER (Observations)).

Temporary Data Table 2:
Hospitalization After a Return to ER (Observations)

| Observation | ln | er7 | h7 | e7h7 |
|---|---|---|---|---|
| 1 | Lxxxxxxxx | 1 | . | . |
| 2 | Lxxxxxxxx | . | 1 | . |
| 3 | Lxxxxxxxx | . | 1 | 1 |
| 4 | Lxxxxxxxx | 1 | . | . |

The present invention may then use a restructuring algorithm such as Algorithm 6 to add the event proxies (e.g., for hospitalization within seven days of an ED visit (h7), a second ED visit within seven days of the the prior visit (er7), and a hospitalization within seven days of a second ED visit (e7h7)) to the analytic data table (e.g. Analytic Data Table 1: Hospital Encounter);

Algorithm 6: Data Restructuring

```
use analytic/hospital_encounters
   sort ln
   merge in using temp/e7h7
       capture drop _merge
       sort ln
       recode e7h7 .=0
       recode er7 .=0
       recode h7 .=0
       keep if en=="ER"
   save analytic/ed,replace
``` and then creates the ED analytic data table (Analytic Data Table 2: ED Table).

Analytic Data Table 2:
ED Table (Variables)

| variable name | storage type | display format | value label |
|---|---|---|---|
| ln | str10 | %10s | |
| mr | str8 | %9s | |
| name | str25 | %25s | |
| adx | str5 | %9s | |
| mor | str1 | %9s | |
| drg | int | %8.0g | |

-continued

Analytic Data Table 2:
ED Table (Variables)

| variable name | storage type | display format | value label |
|---|---|---|---|
| pdx | str5 | %9s | |
| proc1 | double | %10.0g | |
| pdate | str8 | %9s | |
| an | str3 | %9s | |
| mdc | byte | %8.0g | |
| cost | int | %9.0g | |
| chg | float | %9.0g | |
| los | byte | %8.0g | |
| en | str8 | %8.0s | |
| sex | byte | %8.0g | sexfmt |
| disp | byte | %8.0g | disp |
| priority | byte | %8.0g | priority |
| eadate | int | %9.0g | |
| eddate | int | %9.0g | |
| year | int | %9.0g | |
| lid | long | %10.0g | |
| mid | long | %10.0g | |
| phy | float | %9.0g | |
| surg | float | %9.0g | |
| mort | byte | %9.0g | |
| ama | byte | %9.0g | |
| ebdate | int | %9.0g | |
| age | byte | %9.0g | |
| h7 | byte | %9.0g | |
| e7h7 | byte | %9.0g | |
| er7 | byte | %9.0g | |

Each row of Analytic Data Table 2: ED Table represents a single ED encounter. The observations appears as follows:

Analytic Data Table 2: ED Table (Observations)

Observation 1:

| ln | Lxxxxxxx | mr | Mxxxxxxx | name | xxxxxx |
|---|---|---|---|---|---|
| adx | 883.0 | mor | . | drg | . |
| pdx | 883.0 | proc1 | . | pdate | . |
| an | . | mdc | 9 | cost | 289 |
| chg | 378 | los | 1 | sex | M |
| disp | RTN | priority | EM | en | er |
| eadate | −2xxx | eddate | −2xxx | year | 19xx |
| lid | xxxxxxxx | mid | xxxxxx | phy | 38xx0 |
| surg | . | mort | 0 | ama | 0 |
| ebdate | 1xxx | age | 94 | h7 | 0 |
| e7h7 | 1 | er7 | 0 | | |

Example 2

Figure 6:
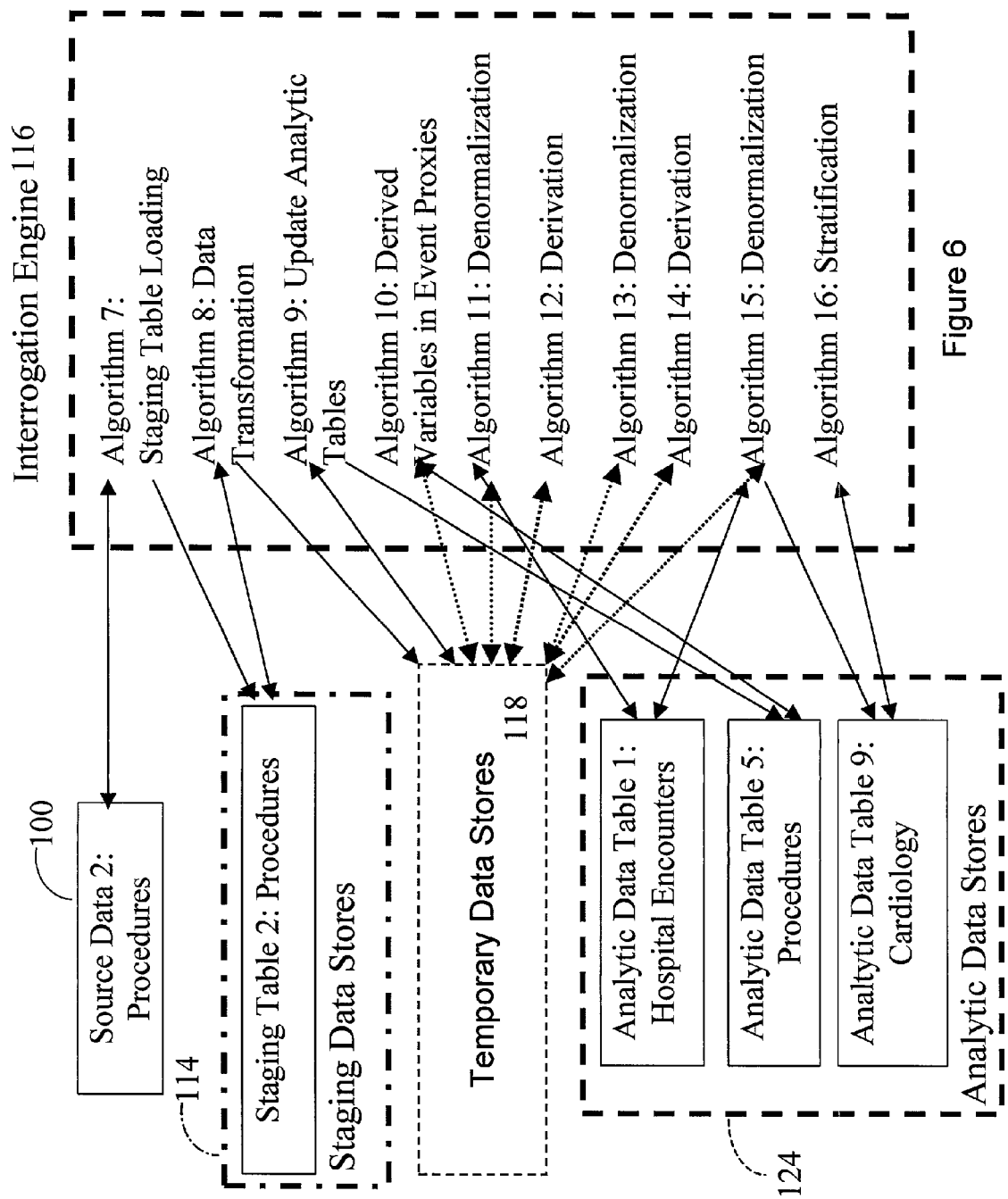
FIG. 6 is a schematic diagram of an exemplary preferred embodiment of the process flow of the interrogation engine used in Example 2.

Example 2 (FIG. 6) demonstrates stratification, another preferred feature of the present invention, in which the present invention has the ability to group (stratify) patients, analyze events by group, and compare groups. Elements of the analytic or staging data stores 124, 114 define stratifications. Events and combinations of events and data elements can also be used to define stratifications. Stratifications are used to define study populations such as patients undergoing coronary artery bypass graft surgeries (CABG), patients with acute myocardial infarction (MI or heart attack), San Francisco surgery patients, hypotensive patients, and hypokalemic patients. Other exemplary predefined stratification groups may include CABG, coronary artery angioplasty, classification by department (Medicine, Surgery, Ob-gyn, Pediatrics, Psychiatry), surgical subspecialty, coronary artery disease, acute MI, respiratory failure, American Society of Anesthesiologists (ASA score), and anesthesia type. Within a study population subpopulations with similar characteristics (e.g., angioplasty associated with acute MI) can be defined. Stratifications may also be useful in comparing outcomes (e.g., outcomes by surgeon, outcomes by hospital, or hypotensive patients with right-heart catheter versus hypotensive patients without right-heart catheter but excluding patients post-CABG).

The present invention allows the user to create new events and stratifications from any suitable variable in the analytic or staging data stores. "Suitable" refers to properties of a variable (e.g. string, numeric, categorical, or continuous) that determine its treatment within the analytic environment. The user may use Boolean statements (e.g. AND, OR, NOR, NOT) to combine variables to form complex stratifications. User-defined stratifications or events can be created by joining pre-defined stratafications and/or events from variables in the staging data store 114 and/or analytic data stores 124. The user can search the analytic or staging data stores 124, 114 for variables to use in stratification or event creation. The user can independently determine the usefulness or relevance of a variable in defining an event or stratification. User-defined events or stratifications can be stored locally for future use and/or made available system-wide. Example 2 illustrates event creation and stratification for the analysis of hospitalized patients having coronary artery disease.

The present invention first loads extracted source data stores such as procedure data flat files (Source Data 2: Procedure Flat File Extract) into procedure staging data stores 114 (Staging Data Table 2: Procedures (Variables) and (Observations)).

| Source Data 2: Procedure Flat File Extract | | | | |
|---|---|---|---|---|
| L011111111 | 10 | 12/17/0x | 33.24 | KXXX |
| L011111111 | 20 | 12/17/0x | | KXXX |
| L011111111 | 30 | 12/17/0x | | KXXX |
| L011111111 | 40 | 12/17/0x | | KXXX |
| L011111111 | 50 | 12/17/0x | | KXXX |
| L011111111 | 60 | 12/17/0x | | KXXX |
| L011111111 | 70 | | | |
| L011111111 | 80 | | | |
| L011111111 | 90 | | | |
| L011111111 | 100 | | | |
| L011111111 | 110 | | | |
| L011111111 | 120 | | | |
| L011111111 | 130 | | | |
| L011111111 | 140 | | 34.09 | |
| L011111111 | 150 | 12/20/0x | 81.91 | FXXX |
| L011111111 | 160 | 12/26/0x | 96.56 | HXXX |
| L011111111 | 170 | 12/11/0x | 36.14 | RXXX |
| L011111111 | 180 | 12/07/0x | 37.23 | DXXX |
| L011111111 | 190 | 12/11/0x | 39.61 | RXXX |
| L011111111 | 200 | 12/11/0x | 39.31 | RXXX |
| L011111111 | 210 | 12/11/0x | 37.61 | RXXX |
| L011111111 | 220 | 12/07/0x | 88.56 | DXXX |
| L011111111 | 230 | 12/12/0x | 34.03 | RXXX |
| L011111111 | 240 | 12/11/0x | 96.71 | UXXX |

Algorithm 7 is another example of a staging data table loading algorithm that loads extracted source data stores 100 into the procedure staging data tables 114. Dictionary 2: Procedures Dictionary maps procedure data (Source Data 2: Procedure Flat File Extract) to the procedure staging data tables (Staging Data Table 2: Procedures (Variables) and (Observations)).

| Dictionary 2: Procedures Dictionary | | | |
|---|---|---|---|
| dictionary { | | | |
| _column(1) | str10 | ln | %10s |
| _column(15) | int | pnumber | %2s |
| _column(18) | str8 | pdate | %8s |
| _column(28) | str5 | proc | %5s |
| _column(36) | str5 | md_init | %9s |
| } | | | |

| Algorithm 7: Staging Data Table Loading |
|---|
| infile using staging/procedures_dictionary,using (staging/Source_Data_2) rename proc proc_str |
| save staging/procedures,replace |

The data now in the procedure staging data tables (Staging Data Table 2: Procedures) has the following variables:

| Staging Data Table 2: Procedures (Variables) | | |
|---|---|---|
| variable name | storage type | display format |
| ln | str10 | %10s |
| pnumber | int | %8.0g |
| pdate | str8 | %9s |
| proc_str | str5 | %9s |
| md_init | str5 | %9s |

The first 10 lines of Source Data 2: Procedure Flat File Extract now appear in the procedure staging data table as Staging Data Table 2: Procedures (observations).

| Staging Data Table 2: Procedures (Observations) Observation 1 | | | | | |
|---|---|---|---|---|---|
| n | pnumber | pdate | proc_ | str | md_init |
| 1 | L0XXXXXX | 20 | 12/07/0X | 88.56 | DXXXX |
| 2 | L0XXXXXX | 80 | 12/07/0X | 37.23 | DXXXX |
| 3 | L0XXXXXX | 0 | 12/11/0X | 39.31 | RXXXX |
| 4 | L0XXXXXX | 10 | 12/11/0X | 37.61 | RXXXX |
| 5 | L0XXXXXX | 40 | 12/11/0X | 96.71 | UXXXX |
| 6 | L0XXXXXX | 70 | 12/11/0X | 36.14 | RXXXX |
| 7 | L0XXXXXX | 90 | 12/11/0X | 39.61 | RXXXX |
| 8 | L0XXXXXX | 30 | 12/12/0X | 34.03 | RXXXX |
| 9 | L0XXXXXX | 10 | 12/17/0X | 33.24 | KXXXX |
| 10 | L0XXXXXX | 20 | 12/17/0X | | KXXXX |

The interrogation engine 116 next uses Algorithm 8, a staged data transformation algorithm, to transform staged procedure data, to fill in missing dates and drop observations without procedural information.

| Algorithm 8: Data Transformation And Cleansing Algorithms |
|---|
| use staging/procedures |
|    gen double proc=real(proc_str) /*create string storage type*/ |
|    gen epdate=date(pdate,"mdy",2010) /*create elapsed date*/ |
|      quietly gen obs=n |

-continued

Algorithm 8: Data Transformation And Cleansing Algorithms sort ln obs
    quietly by ln:replace epdate=epdate[_n-1] if epdate==.
/*fill in missing dates*/
    drop obs
drop pdate
drop proc_str
drop if proc==. /*drop observation if no procedure number*/
sort ln epdate pnumber
    save temp/procedures Following Algorithm 8, the data is in procedure analytic data store format. Algorithm 8: Data Transformation And Cleansing Algorithms may then save the data in a temporary data table 118. Algorithm 9: Update Analytic Tables, an optional analytic data store update algorithm, may be used to update the analytic data store 124 to produce an updated procedure analytic data table (Analytic Data Table 3: Procedures). Algorithm 9 may do this by adding new procedure data from the temporary procedure table created by Algorithm 8 to Analytic Data Table 3: Procedures, with the following variables:

| Analytic Data Table 3: Procedures (Variables) | | |
|---|---|---|
| variable name | storage type | display format |
| ln | str10 | %10s |
| pnumber | int | %8.0g |
| md_init | str5 | %9s |
| proc | double | %10.0g |
| epdate | float | %9.0g |

| Algorithm 9: Update Analytic Data Tables |
|---|
| use temp/procedures |
|     sort ln epdate pnumber |
|     merge ln epdate pnumber using analytic/procedures,update replace |
|     save analytic/procedures,replace |

The Staging Data Table 2: Procedures (Observations) now appear in Analytic Data Table 3: Procedures as observations. The date (pdate) is now encoded as an elapsed date, and in this example of Analytic Data Table 3: Procedures, is displayed as a coded storage number rather than the date that it represents.

| Analytic Data Table 3: Procedures (Observations) Observation 1: | | | | | |
|---|---|---|---|---|---|
| n | pnumber | pdate | proc | str | md_init |
| 1 | L0xxxxxxxx | 20 | 1495 | 88.56 | Dxxxx |
| 2 | L0xxxxxxxx | 80 | 1495 | 37.23 | Dxxxx |
| 3 | L0xxxxxxxx | 0 | 1495 | 39.31 | Rxxxx |
| 4 | L0xxxxxxxx | 10 | 1495 | 37.61 | Rxxxx |
| 5 | L0xxxxxxxx | 40 | 1495 | 96.71 | Uxxxx |
| 6 | L0xxxxxxxx | 70 | 1495 | 36.14 | Rxxxx |
| 7 | L0xxxxxxxx | 90 | 1495 | 39.61 | Rxxxx |
| 8 | L0xxxxxxxx | 30 | 1495 | 34.03 | Rxxxx |
| 9 | L0xxxxxxxx | 10 | 1496 | 33.24 | Kxxxx |

Algorithm 10: Derived Variables: Identify Event Proxies is an exemplary algorithm for deriving variables and creating event proxies. In this example, Algorithm 10: Derived Variables: Identify Event Proxies acts on Analytic Data Table 3: Procedures and creates derived variables that are event proxies for: CABG, valve replacement, coronary angioplasty, and intra-coronary stent placement. Algorithm 10: Derived Variables: Identify Event Proxies initially creates a temporary data table (e.g. Temporary Data Table 3: Cardiovascular Procedures) keeping procedure observations corresponding to the selected cardiovascular procedures.

| Algorithm 10: Derived Variables: Identify Event Proxies |
|---|
| use analytic/procedures |
|     gen cabg=(proc>36.09&proc<36.9) |
|     gen valve=(proc>34.99&proc<36.00) |
|     gen angioplasty=(proc>36.01&proc<36.1) |
|     gen ptca=(proc==36.01\|proc==36.02\|proc==36.05\|proc==36.09) |
|     gen stent=(proc==36.06) |
|     gen balloon=(proc>=37.60&proc<37.7) /*intra-aortic balloon pump use*/ |
|     keep if ptca==1\|cabg==1\|stent==1\|balloon==1\|angioplasty==1 |
|     capture drop ttype x |
|     gen ttype=1 if ptca==1 |
|     replace ttype=2 if cabg==1 |
|     sort ln |
|     capture drop_merge |
| save temp/cardiovascular_procedures,replace |

Temporary Data Table 3: Cardiovascular Procedures has the following variables:

| Temporary Data Table 3: Cardiovascular Procedures (Variables) | | |
|---|---|---|
| variable name | storage type | display format |
| ln | str10 | %10s |
| pnumber | int | %8.0g |
| md_init | str5 | %9s |
| epdate | float | %9.0g |
| proc | double | %10.0g |
| cabg | float | %9.0g |
| valve | float | %9.0g |
| angioplasty | float | %9.0g |
| ptca | float | %9.0g |
| stent | float | %9.0g |
| balloon | float | %9.0g |
| ttype | float | %9.0g |

From Analytic Data Table 3, Procedures, Algorithm 10: Derived Variables: Identify Event Proxies has identified two (2) cardiovascular events shown below in Temporary Data Table 3: Cardiovascular Procedures (Observations) from the twelve (12) procedures derived from the example data in Source Data 2: Procedure Flat File Extract.

| Temporary Data Table 3: Cardiovascular Procedures (Observations) | | | | | |
|---|---|---|---|---|---|
| Observation 1: | | | | | |
| ln | Lxxxxxxx | pnumber | 70 | md_init | Rxxxxx |
| epdate | 1xxxx | proc | 36.14 | cabg | 1 |
| valve | 0 | angiop~y | 0 | ptca | 0 |
| stent | 0 | balloon | 0 | ttype | 2 |

-continued

Temporary Data Table 3: Cardiovascular Procedures (Observations)

Observation 2:

| ln | Lxxxxxxx | pnumber | 10 | md_init | Rxxxx |
|---|---|---|---|---|---|
| epdate | 1xxxx | proc | 37.61 | cabg | 0 |
| valve | 0 | angiop~y | 0 | ptca | 0 |
| stent | 0 | balloon | 1 | ttype | . |

Algorithm 11: Denormalization—Join Tables is a denormalization algorithm that joins data (medical record numbers (mr) admission (eadate) and discharge (eddate) dates) from the hospital encounter table (Analytic Data Table 1: Hospital Encounters) to Temporary Data Table 3: Cardiovascular Procedures.

Algorithm 11: Denormalization - Join Tables

```
use analytic/hospital_encounters
    keep mid ln eddate eadate los
    sort ln
    merge ln using temp/cardiovascular_procedures
    keep if_merge==3
    save temp/cardiovascular_procedures,replace
```

For the observations illustrated above the algorithm would extract the following data from Analytic Data Table 1: Hospital Encounters: "ln Lxxxxxxx los 28 eadate 05decxxxx eddate 02janxxxx mid 9xxxxxx." Algorithm 11: Denormalization—Join Tables then joins this information to the corresponding observations in Temporary Data Table 3: Cardiovascular Procedures. Temporary Data Table 3: Cardiovascular Procedures now has additional data which is emphasized in the table below.

Temporary Data Table 3: Cardiovascular Procedures (Observations)

Observation 1:

| ln | Lxxxxxxxx | pnumber | 70 | md_init | Rxxxx |
|---|---|---|---|---|---|
| epdate | 11decxxxxx | proc | 36.14 | cabg | 1 |
| valve | 0 | angiop~y | 0 | ptca | 0 |
| stent | 0 | balloon | 0 | ttype | 2 |
| los | 28 | eadate | 05decxxxxx | eddate | 02janxxxx |
| mid | 9xxxxxx | | | | |

Temporary Data Table 3: Cardiovascular Procedures (Observations)

Observation 2:

| ln | Lxxxxxxxx | pnumber | 10 | md_init | Rxxxxx |
|---|---|---|---|---|---|
| epdate | 11decxxxxx | proc | 37.61 | cabg | 0 |
| valve | 0 | angiop~y | 0 | ptca | 0 |
| stent | 0 | balloon | 1 | ttype | . |
| los | 28 | eadate | 05decxxxx | eddate | 02janxxxxx |
| mid | 9xxxxxx | | | | |

Algorithm 12: Derivation—Event Dates is an exemplary derivation algorithm that derives date markers and time relationships between the cardiovascular procedures; and identifies the physician performing the first angioplasty/stent procedures of a hospital admission.

Algorithm 12: Derivation - Event Dates

```
use temp/cardiovascular_procedures
    gen angio_dte=epdate if angioplasty==1
    egen angio_dte1=min(angio_dte),by(ln)
    egen angio_dte2=max(angio_dte),by(ln)
    gen cabg_dte=epdate if cabg==1
    egen cabg_dte1=min(cabg_dte),by(ln)
    replace angioplasty=.if angioplasty==0
    sort ln angioplasty epdate
    gen str8 angio_md=md_init if angioplasty==1
    gen str8 stent_md=md init if stent==1
    quietly by ln:replace angio_md=angio_md[1]
    replace stent=. if stent==0
    sort ln stent epdate
    quietly by ln:replace stent_md=stent_md[1]
    replace angioplasty=0 if angioplasty==.
    replace stent=0 if stent==.
    drop angio_dte
    replace cabg==. if cabg==0
    sort ln cabg epdate
    gen str8 cabg_md=md_init if cabg==1
    quietly by ln:replace cabg_md=cabgmd[1]
    replace cabg==0 if cabg==.
    drop cabg_dte
    rename cabg_dte1 cabg_dte
    save,temp/cardiovascular_procedures,replace
```

The observations in Temporary Data Table 3: Cardiovascular Procedures now appear with new derived data elements which are emphasized in the table below.

Temporary Data Table 3: Cardiovascular Procedures (Observations)

Observation 1:

| ln | Lxxxxxxxx | pnumber | 70 | md_init | Rxxxxx |
|---|---|---|---|---|---|
| epdate | 11decxxx | proc | 36.14 | cabg | 1 |
| valve | 0 | angiop~y | 0 | ptca | 0 |
| stent | 0 | balloon | 0 | ttype | 2 |
| los | 28 | eadate | 05decxxxx | eddate | 02janxxxxx |
| mid | 9xxxxxx | angio_~1 | . | angio_~2 | . |
| cabg_dte | 11decxxxx | angio_md | | stent—md | |
| cabg_md | Rxxxxxx | | | | |

Observation 2:

| ln | Lxxxxxxxx | pnumber | 10 | md_init | Rxxxxx |
|---|---|---|---|---|---|
| epdate | 11decxxx | proc | 37.61 | cabg | 0 |

| Temporary Data Table 3: Cardiovascular Procedures (Observations) | | | | | |
|---|---|---|---|---|---|
| valve | 0 | angiop~y | 0 | ptca | 0 |
| stent | 0 | balloon | 1 | ttype | . |
| los | 28 | eadate | 0xdecxxxx | eddate | 0xjanxxxx |
| mid | 9xxxxxxx | angio_~1 | . | angio_~2 | . |
| cabg_dte | . | angio_md | | stent_md | |
| cabg_md | | | | | |

In many cases an analyst will choose to assess clinical outcomes of cardiovascular procedures based on events occurring on the same day, or during a single hospitalization event. In this case the unit of analysis (denominator) will be represented by an analytic data table where each row represents a procedural day, or in the second case a single hospitalization event. For any given procedural day or hospitalization event, there may be any number (zero to many) of cardiovascular procedures. Algorithm 13: Denormalization is a denormalization algorithm, and summarizes the cardiovascular procedure table to one row (observation)=one procedure date (i.e. all procedures occurring on a particular day are represented as a single observation.

Algorithm 13: Denormalization (Summarization)

```
use temp/cardiovascular_procedures
    egen lstent=max(stent),by(ln epdate)
    egen lptca=max(ptca),by(ln epdate)
    egen lcabg=max(cabg),by(ln epdate)
    egen lbal=max(balloon),by(ln epdate)
    egen langioplasty=max(angioplasty),by(ln epdate)
    drop stent ptca cabg balloon angioplasty
    drop pnumber pdate md_init proc
    sort ln epdate
    quietly by ln epdate:keep if_n==1
    rename lstent stent
    rename lptca ptca
    rename lcabg cabg
    rename lbal balloon
    rename langioplasty angioplasty
save temp/cardiovascular_procedures_day
```

Since Observations 1 and 2 of this example occur on the same day, they are summarized as procedure events ("cabg," "balloon," "stent," "ptca," and "angioplasty") occurring within a single observation summarizing each day's cardiovascular procedures in Temporary Data Table 4: Cardiovascular Procedures By Day (emphasized).

Temporary Data Table 4: Cardiovascular Procedures By Day (Observations)

Observation 1:

| ln | Lxxxxxxx | epdate | 1495 | eadate | 1494 |
|---|---|---|---|---|---|
| stent | 0 | ptca | 0 | cabg | 1 |
| balloon | 1 | | | | |
| angioplasty | . | | | | |

Algorithm 14: Derivation is a derivation algorithm and creates the event proxies identifying: intra-aortic balloon pump placement day of admission, procedure failure; second angioplasty in 6 months (angio180), CABG within six months after angioplasty(cabg180); and high utilization: two angioplasties same admission (angioplasty2).

Algorithm 14: Derivation (Event Proxies)

```
use temp/cardiovascular_procedures_day
    sort ln epdate
    quietly by ln:gen bal_adm=1 if balloon==1&epdate==eadate
    sort mid epdate ttype
    quietly by mid:gen redoc=1 if epdate[_n+1]-
epdate<=180&epdate[_n+1]-epdate~=.&epdate[_n+1]>eddate
    quietly by mid:gen angio180=1 if (epdate[_n+1]-
epdate<=180&epdate[_n+1]-epdate~=.&epdate[_n+1]>
eddate)&angioplasty[_n+1]==1
    quietly by mid:gen cabg180=1 if (epdate[_n+1]-
epdate<=180&epdate[_n+1]-epdate~=.&epdate[_n+1]>
eddate)&cabg[_n+1]==1
    quietly by mid:gen angioplasty2-1 if
epdate[_n+1]<=eddate&angioplasty[_n+1]==1
    quietly by mid:gen ccabg=1 if
angioplasty==1|stent==1&epdate[_n+1]<=eddate)&cabg[_n+1]==1
    replace ccabg=0 if ccabg==.&ptca==1
        replace angioplasty2=0 if angioplasty2==.& angioplasty==1
        replace redoc=0 if redoc==.&angioplasty==1
        replace stent=0 if stent==.&angioplasty==1
        replace angio180=0 if angio180==.&angioplasty==1
        replace cabg180=0 if cabg180==.&angioplasty==1
save temp/cardiovascular_procedures_day
```

Observation 1 from Temporary Data Table 4: Cardiovascular Procedures By Day now appears with new derived variables (event proxies) that are emphasized in bold.

Temporary Data Table 4: Cardiovascular Procedures By Day (Observations)

Observation 1:

| ln | Lxxxxxxx | epdate | 1495 | los | 28 |
|---|---|---|---|---|---|
| eadate | 1494 | eddate | 1497 | stent | 0 |
| ptca | 0 | cabg | 1 | balloon | 1 |
| angiop~y | 0 | bal_adm | . | bal1 | . |
| redoc | . | angio180 | . | cabg180 | . |
| angiop~2 | . | ccabg | . | | |

Algorithm 15 (Part 1): Denormalization is a denormalization algorithm of the algorithm that extracts, summarizes, and saves physician identifiers from the cardiovascular procedure table.

Algorithm 15 (Part 1): Denormalization

```
use temp/cardiovascular_procedures
    sort ln
    quietly by ln:keep if_n==1 /*summarize to cardiovascular
        hospitalization
        by keeping only the first cardiovascular procedure of the
            hospitalization*/
```

Algorithm 15 (Part 3): Denormalization joins the physician identifiers and procedure dates saved in Data Table 5: Cardiovascular Procedure Physician Identifiers by Algorithm 15 (Part 1): Denormalization to Temporary Data Table 6: Cardiovascular Procedures By Hospitalization.

| Algorithm 15 (Part 1): Denormalization |
|---|
| keep ln angio_md angio_dte1 angio_dte2 stent_md cabg_dte cabg_md<br>/*save information identifying the patient hospitalization event, and physician identifiers for the cardiovascular procedures and procedure dates*/<br>sort ln<br>save temp/cv_md_dates,replace |

This would result in the following observations created in Temporary Data Table 5: Cardiovascular Procedure Physician Identifiers.

| Temporary Data Table 5:<br>Cardiovascular Procedure<br>Physician Identifiers (Observations)<br>Observation 1: | | | | | |
|---|---|---|---|---|---|
| ln | Lxxxxxxx | angio_dte1 | . | angio_dte2 | . |
| cabg_dte | 11decxxxx | angio_md | | stent_md | |
| cabg_md | Rxxxxxx | | | | |

Algorithm 15 (Part 2): Denormalization summarizes the cardiovascular procedure day table to a single patient-hospitalization event.

| Algorithm 15 (Part 2): Denormalization |
|---|
| use temp/cardiovascular_procedures_day<br>    collapse (max) ptca angioplasty balloon stent cabg ccabg redoc<br>        angioplasty2 angio180 cabg180 ball bal_adm (mean)<br>        mid, by (ln)<br>    recode redoc .=0<br>    recode cabg .=0<br>    recode angioplasty2 .=0<br>    recode ccabg .=0<br>    recode balloon .=0<br>    sort ln<br>    quietly by ln:assert_N==1<br>save temp/cardiovascular_procedures_hospitalization |

Observation 1 from Temporary Data Table 4: Cardiovascular Procedures By Day is not significantly changed as there is only one observation for that hospitalization—if there were multiple cardiovascular procedures on different days of the same hospitalization they would now all be represented as a single observation in Temporary Data Table 6: Cardiovascular Procedures By Hospitalization.

| Temporary Data Table 6: Cardiovascular Procedures By Hospitalization (Observations) | | | | | |
|---|---|---|---|---|---|
| Observation 1: | | | | | |
| ln | Lxxxxxxx | ptca | 0 | angiop~y | 0 |
| balloon | 1 | stent | 0 | cabg | 1 |
| ccabg | 0 | redoc | 0 | angiop~2 | 0 |
| angio180 | . | cabg180 | . | ball | . |
| bal_adm | . | mid | 9xxxxxxx | | |

| Algorithm 15: Denormalization (Part 3) |
|---|
| use temp/cardiovascular_procedures_hospitalization<br>    capture drop_merge<br>    merge ln using temp/cv_md_dates<br>    capture drop_merge<br>    sort ln<br>    quietly by ln:assert_N==1<br>    save temp/cardiovascular_procedures_hospitalization |

Observation 1 in Temporary Data Table 6: Cardiovascular Procedures By Hospitalization, now has the following variables (additions are emphasized).

| Temporary Data Table 6: Cardiovascular Procedures By Hospitalization (Observations) | | | | | |
|---|---|---|---|---|---|
| Observation 1: | | | | | |
| ln | Lxxxxxxx | ptca | 0 | angiop~y | 0 |
| balloon | 1 | stent | 0 | cabg | 1 |
| ccabg | 0 | redoc | 0 | angiop~2 | 0 |
| angio180 | . | cabg180 | . | ball | . |
| bal_adm | . | mid | 9xxxxxxx | angio_dte1 | . |
| angio_dte2 | . | cabg_dte | 11decxxxx | angio_md | |
| stent_md | . | cabg_md | Rxxxxxx | | |

Algorithm 15 (Part 4): Denormalization joins Temporary Data Table 6: Cardiovascular Procedures By Hospitalization to Analytic Data Table 1: Hospital Encounters creating Analytic Data Table 4: Cardiology.

| Algorithm 15 (Part 4): Denormalization |
|---|
| use analtyic/hospital_encounters<br>    keep if en="hosp"<br>    sort in<br>    merge ln using temp/cardiovascular_procedures_hospitalizaiton<br>        save analytic/cardiology |

Algorithm 15 (Part 4): Denormalization first interrogates Analytic Data Table 1: Hospital Encounters, representing hospitalization encounters, and then combines data matched by unique hospitalization event identifiers (ln) by interrogating and adding to Analytic Data Table 1: Hospital Encounters, cardiovascular procedures by hospitalization. Algorithm 15 (Part 4): Denormalization completes the denormalization process, by which the present invention restructures, derrives and summarizes information from Analytic Data Table 1: Hospital Encounters and Analytic Data Table 3: Procedures, and in this process creates Analytic Data Table 4: Cardiology with the following variables and exemplary observations.

Analytic Data Table 4: Cardiology (Observations)

Observation 1:

| | | | | | |
|---|---|---|---|---|---|
| sex | M | mor | . | drg | 107 |
| phy | 3xxxxxx | surg | 3xxxxx | mdc | 5 |
| cost | 84375 | chg | 402838 | los | 28 |
| year | xxxx | time | Janxx | eadate | 1494 |
| eddate | 1497x | epdate | 1496x | mrn | . |
| priority | EM | disp | RTN | mod | 0 |
| anesth | . | age | 73 | dx | 428 |
| admdx | 518.4 | proc1 | 33.24 | fy | . |
| ebdate | −1174 | type | | surg | |
| ama | 0 | indate | 1494 | outdate | . |
| indate2 | . | outdate2 | . | icu | 1 |
| iculos | . | name | xxxxxxxxxx | an | . |
| hlc | 0 | mr | Mxxxxxxxxx | mdno | . |
| mid | 9xxxxxxx | fname | | flag | . |
| flag2 | . | flag3 | . | ln | Lxxxxxxxxxx |
| ptca | 0 | angioplastyy | 0 | balloon | 1 |
| stent | 0 | cabg | 1 | ccabg | 0 |
| redoc | 0 | angioplasty2 | 0 | | |
| angio180 | . | cabg180 | . | bal1 | . |
| bal_adm | . | angio_dte1 | . | angio_dte2 | . |
| cabg_dte | 11decxxxx | angio_md | . | stent_md | . |
| cabg_md | Rxxxxxx | | | | |

Algorithm 16: Stratification is a stratification algorithm based on acuity of the coronary lesion identifying (stratifying) a very high risk patient group—those with an acute myocardial infarction (heart attack).

Algorithm 16: Stratification

```
use analytic/cardiology
    gen grp=1 if (dx>409.9&dx<410.7)|(dx>410.79&dx<411)
    replace grp=2 if dx>410.69&dx<410.8
    replace grp=3 if dx>410.99&dx<411.89
    replace grp=4 if dx>411.9&dx<415
    label def grp 1 "AMI" 2 "SEMI" 3 "Unstable" 4 "Angina"
    lab val grp grp
    gen ami=(grp==1|grp==2)
    sort ln
        save analytic/cardiology,replace
```

The following stratification variables (emphasized) now appear in the observations found in Analytic Data Table 4: Cardiology.

Analytic Data Table 4: Cardiology (Observations)

| | | | | | |
|---|---|---|---|---|---|
| sex | M | mor | . | drg | 107 |
| phy | 3xxxxxx | surg | 3xxxxx | mdc | 5 |
| cost | 84375 | chg | 402838 | los | 28 |
| year | xxxx | time | Janxx | eadate | 1494 |
| eddate | 1497x | epdate | 1496x | | |
| mrn | . | priority | EM | disp | RTN |
| mort | 0 | anesth | . | age | 73 |
| dx | 428 | admdx | 518.4 | proc1 | 33.24 |
| fy | . | ebdate | −1174 | type | |
| surg | | ama | 0 | indate | 1494 |
| outdate | . | indate2 | . | outdate2 | . |
| icu | 1 | iculos | . | name | xxxxxxxxxx |
| an | . | hlc | 0 | mr | Mxxxxxxxxx |
| mdno | . | mid | 9xxxxxxx | fname | |
| flag | . | flag2 | . | flag3 | . |
| ln | Lxxxxxxxxxx | ptca | 0 | angiop~y | 0 |
| balloon | 1 | stent | 0 | cabg | 1 |

-continued
Analytic Data Table 4: Cardiology (Observations)

| | | | | | |
|---|---|---|---|---|---|
| ccabg | 0 | redoc | 0 | angiop~2 | 0 |
| angio180 | . | cabg180 | . | bal1 | . |
| bal_adm | . | angio_~1 | . | angio_~2 | . |
| cabg_dte | 11decxxxx | angio_md | | stent_md | . |
| cabg_md | Rxxxxxx | grp | CHF | ami | . |
| interv~n | 1 | | | | |

Queries and User Interface

The analytic environment provides for the analysis of events, the stratification of patients, and the ability to discover and pose new questions. The present invention enables users to ask clinical questions of a data warehouse without being limited to pre-defined questions. This is a significant advantage over the structured queries available in known systems. Specifically, the present invention allows a user to independently author ad hoc queries.

As new questions frequently arise in the process of analyzing analytic or staging data stores 124, 114, the present invention supports the intermediate and advanced user in independently writing new queries to address questions not currently handled by the system. The design of the present invention's interrogation engine 116, and analytic data stores 124 ensure high performance query response times for independent ad hoc queries even in the face of analytic or staging data stores 124, 114.

To author independent queries, the present invention preferably relies on a command line or browser based graphical user interface (GUI) (User Interface 126). Working from the GUI, the present invention allows the user to create new queries from any suitable variable(s) in analytic or staging data stores 124, 114. Suitable refers to properties of a variable (e.g. string, numeric, categorical, continuous) that determine its treatment within the analytic environment. The user of the present invention may use Boolean statements (e.g. AND (&), OR, NOR, or NOT) to combine variables to form complex stratifications. User defined stratifications or events can be created by joining pre-defined stratifications, events, and/or from variables in the analytic or staging data stores 124, 114. Drop down boxes list pre-defined stratifiers, events, and variables commonly used in event creation or stratification (e.g. admission diagnosis, principal diagnosis, procedure (ICD9 or CPT), DRG, medical center, age, attending physician, surgeon, mortality, or re-intubation), and provide for the entry of a specific value, or range of values (procedure=36.01, 36≦procedure<37). The user of the present invention can search the analytic or staging data stores 124, 114 for variables to use in stratification or event creation. The user of the present invention can independently determine the usefulness or ability of a variable in defining an event or stratification. User defined events or stratifications can be stored locally for future use and/or made available system wide.

Event analysis GUI

The analytic interrogation engine 116 of the present invention takes advantage of pre-defined events (ccabg) and groups (e.g. stent or ami) found in the analytic data tables 124 but does not require them. An example of an ad hoc query is the analysis of the impact of stent utilization on the number of patients with coronary artery by-pass surgery following coronary angioplasty for acute myocardial infarction. This measure is a proxy for a post-angioplasty complication: abrupt vessel closure. In this example, the interrogation engine 116 would utilize Analytic Data Table 4: Cardiology as created in Example 2 above with the following pre-defined variables: angioplasty, ami, stent, and ccabg. The present invention would begin this analysis in the event analysis window with the following:

| GUI 1: Event Analysis, CABG Following Angioplasty |
| --- |
| 1. Analytic table = *hospital_encounters* |
| 2. Start event = *angioplasty* |
| 3. End event = *angioplasty* |
| 4. Define study group = *ami* |
| 5. Compare by = *stent* |
| 6. Comparison value = *ccabg* |
| 7. Statistic/method = *means with 95% CI (categorical)* |
| 8. Graph/table = *graph* |
| 9. Save results tables = *abrupt vessel closure* |
| 10. Run Analysis |

"Run Analysis" would parse the GUI choices (input) to Algorithm 17: Event Analysis which would, in turn, produce and run Interrogation Script 1: Abrupt Vessel Closure.

| Algorithm 17: Event Analysis |
| --- |
| use analytic/"analytic table," clear |
| keep if "event name"==1 |
| keep if "study group expression"==1 |
| "graph" "x-axis variable" "y-axis variable" |
| save usr/"results table" |

The interrogation engine 116 may then parse analytic data table choice "hospitalization events" as the object of use in line 1 of Algorithm 17: Event Analysis resulting in Interrogation Script 1: Abrupt Vessel Closure.

| Interrogation Script 1: Abrupt Vessel Closure |
| --- |
| use analytic/*hospital_encounter*, clear |
| keep if *angioplasty*==1 |
| keep if *ami*==1 |
| catcibi stent ccabg |
| save usr/*abrupt vessel closure* |

By substituting different variables in GUI 1: Event Analysis, CABG Following Angioplasty, line 4 (define study group), line 5 (define comparison grouping), and line 6 (define comparison statistic); a variety of outcome measures and stratification can be easily created: e.g. abrupt vessel closure by performing physician, mortality by performing physician, mortality by stent usage.

If an event is represented in the staging data tables, the analytic interrogation engine 116 can either create the event from existing values in the analytic data tables 124 or if required address the staging data tables 114 and create a new analytic data table with the appropriate values. For example, one could substitute the following for GUI 1: Event Analysis, CABG Following Angioplasty, line 4 above to create the acute MI study group:

4. Define study group=(dx>409.9&dx<410.7)| (dx>410.79&dx<411)

"dx" refers to the standard principal diagnosis variable found in Analytic Data Table 1: Hospital Encounters. The numeric range is the standard diagnostic code (ICD9) values for an acute myocardial infarction.

Event Creation GUI

If for example, the variable representing coronary artery by-pass surgery following angioplasty (ccabg) was not previously created, the user of the present invention would use GUI 2: Event Creation, CABG Following Angioplasty to create the "ccabg" value.

| GUI 2: Event Creation, CABG Following Angioplasty |
| --- |
| 1. Analytic Data Table 1 = *procedures* |
| 2. Episode = *1* (1=first, _N=last, default = all) |
| 3. Event1 = *(proc>=36.01&proc<36.1)* - coronary angioplasty |
| 4. Event1 value = *none* |
| 5. Event1 duration = *none* |
| 6. Event2 =(proc>36.09&proc<36.9) - coronary by-pass surgery |
| 7. Event2 value = *none* |
| 8. Event2 duration = *none* |
| 9. Interval between event 1 and event 2 = *>=0* |
| 10. Save results table = *ccabg* |
| 11. Analytic Data Table 2 = *hospital_encounters* |
| 12. New Analytic Data Table = *abrupt vessel closure* |
| 13. New variable name = *ccabg* |
| 14. Run Analysis |

The code "Run Analysis" would parse the GUI values (shown in italics) to Algorithm 18 (Part 1): Create Event:

| Algorithm 18 (Part 1): Create Event |
| --- |
| use analytic/'Analytic Data Table 1' |
|    if episode=="all" { |
|       gen event=1 if event1>*105&event1*~=. |
|       sort ln date time event |
|       quietly by ln:gen episode=1 if event[_n1]==.&event==1 |

---
Algorithm 18 (Part 1): Create Event
---

```
    quietly by ln:gen epi_n=sum(episode)
    replace epi_n=. if event==.
    sort ln epi_n date time
    by ln epi_n:gen epi_time=(time[_N]-time[1]) if
date[_N]==date[1]
    compress
    egen epi_median=median(event1),by(ln epi_n)
    egen epi_max=max(event1),by(ln epi_n)
    egen epi_mean=mean(event1),by(ln epi_n)
    by ln epi_n:gen epi_time1=time[1]
    by ln epi_n:gen epi_timeN=time[N]
    by ln epi_n:gen epi_date1=date[1]
    by ln epi_n:gen epi_dateN=date[_N]
    sort ln epi_n
    quietly by ln epi_n:keep if_n==1
    drop if epi_n==.
    drop if epi_time<5
    drop if epi_time==.
    quietly by ln: gen n=_N
    egen time_total=sum(epi_time),by(ln)
    sort ln epi_time
    quietly by ln:keep if_n==_N
    keep epi*
    }
else {
    gen event=1 if 'event1'==1
    replace event=2 if 'event2'==1
    keep if event~=.
    sort ln event event_date
    quietly by ln event:keep if n=='occurrences'
    quietly by ln:gen interval=(event_date[_n+1]-event_date)
    quietly by ln:gen 'new variable'=
(event==1&event[_n+1]==2&interval= 'interval between event 1
and event 2 value'
    keep if 'new variable'==1
    keep ln 'new variable'interval
    }
sort ln
save usr/'save result table'
``` and produce the following interrogation script:

---
Interrogation Script 2: CABG After Angioplasty
---

```
use analytic/procedure_events
    gen event=1 if (proc>=36.01&proc<36.1==1
    replace event=2 if (proc>36.09&proc<36.9) ==1
    keep if event~=.
sort ln event event_date
    quietly by ln event:keep if_n==1
    quietly by ln:gen interval=(event_date[_n+1]event_date)
    quietly by ln:gen ccabg = (event==1&event[_n+1]==2)&interval
>=0&interval~=.
    keep if ccabg ==1
    keep ln ccabg interval
sort ln
save usr/ccabg
```

Interrogation Script 2: CABG After Angioplasty would interrogate Analytic Data Table 3: Procedures which, in this example, might have observations such as the following:

---
Analytic Data Table 3:
Procedures (Observations)
---

Observation 1:

| ln | L00123456 | pnumber 1 | mdinit xxxx |
|---|---|---|---|
| epdate | 1xxx7 | proc 36.11 | |

Observation 2:

| ln | L00123456 | pnumber 2 | mdinit xxxx |
|---|---|---|---|
| epdate | 1xxx7 | proc 36.15 | |

Observation 3:

| ln | L00123456 | pnumber 1 | mdinit aaaaa |
|---|---|---|---|
| epdate | 1xxx6 | proc 36.01 | |

Observation 4:

| ln | L00123456 | pnumber2 | mdinit aaaaa |
|---|---|---|---|
| epdate | 1xxx6 | proc 36.06 | |

Interrogation Script 2: CABG After Angioplasty interrogates Analytic Data Table 3: Procedures and creates an analytic table with the following observations:

---
Analytic Data Table 5: User Results, ccabg
---

| ln L00123456 | ccabg 1 | interval 1 |
|---|---|---|

The interrogation algorithm continues (Algorithm 18 (Part 2): Create Event) and joins Analytic Data Table 5: User Results, ccabg to Analytic Data Table 1: Hospital Encounters creating a new "user defined analytic data table," Analytic Data Table 6: Abrupt Vessel Closure.

---
Algorithm 18 (Part 2): Create Event
---

```
use analytic/'Analytic Data Table 2'
sort ln
merge ln using 'save results table'
drop if_merge==2
sort ln
quietly by ln:assert_N==1
capture drop_merge
save usr/'Analytic Data Table'
```

---
Analytic Data Table 6: Abrupt Vessel Closure (Observations)
---

Observation 1:

| | | | | | |
|---|---|---|---|---|---|
| sex | M | mor | . | drg | 106 |
| phy | 3xxxx | surg | 3xxxxx | mdc | 5 |
| cost | 34978 | chg | 89482 | los | 9 |
| month | 6 | year | xxxx | time | Junxx |
| eadate | 1xxxxx5 | eddate | 1xxxx4 | epdate | 1xxxx7 |
| lid | 123456 | mm | xxxxxxxx | priority | EL |
| disp | SNF | mort | 0 | anesth | GEN |
| age | 72 | dx | 414 | admdx | 414 |
| proc1 | 36.11 | fy | xxxx | ebdate | -xxxxx |
| type | surg | ama | 0 | indate | xxxx |
| outdate | xxxxx | indate2 | . | outdate2 | . |
| icu | 1 | iculos | 4 | name | . |
| an | | hic | 1 | mr | |
| mdno | xxxx | mid | . | ln | L00123456 |
| ccabg | 1 | interval | 1 | | |

The user defined analytic data can now be used for event analysis using the event analysis GUI (GUI 1: Event Analysis, CABG Following Angioplasty) to determine frequency of event (Results Table 1: Abrupt Vessel Closure By Stent Usage), identify high risk populations, or one of a number of event based outcomes; e.g. mortality, cost, volume, event rate (Results Table 2: Abrupt Vessel Closure Outcomes). In Results Table 1: Abrupt Vessel Closure By Stent Usage, the "Stent" column value differentiates patients with acute myocardial infraction undergoing coronary angioplasty with (stent value="1") and without (stent value="2") the use of intra-coronary stent devices. "cm" is the group mean rate of the proxy event for abrupt vessel closure (coronary artery by-pass surgery following coronary artery surgery) for each group (stent=0, and stent=1). "cu" and "cl" define the 95% confidence limits bounding each mean. This table indicates that 7.5% of patients with an acute myocardial infarction having angioplasty without intra-coronary stent placement subsequently require open heart surgery and coronary artery by-pass graft surgery during the same hospital stay; comparred to only 1.9% of patients with stent placement. Examination of the 95% confidence limits indicates that a wide statistical separation and high likelyhood that these values are statitistically signicant.

Results Table 1:
Abrupt Vessel Closure By Stent Usage

| stent | rate ccabg | upper CI | lower CI |
|---|---|---|---|
| 0 | .075 | .108 | .050 |
| 1 | .019 | .040 | .007 |

The user might then determine if there is a clinical or financial difference associated with the event (abrupt vessel closure) or its proxy (coronary artery by-pass surgery after angioplasty). Using GUI 1: Event Analysis, CABG Following Angioplasty, the user may determine these results that are summarized in results Results Table 2: Abrupt Vessel Closure Outcomes. Results Table 2: Abrupt Vessel Closure Outcomes shows the outcomes for 687 patients with an acute MI treated with coronary angioplasty. The twenty-four (24) patients with coronary artery by-pass surgery following angioplasty had a mortality rate of 13%, a 16 day stay, and an average cost of $72,000 per case compared to the 663 patients who did not have the complication (who had lower mortality (5%), a shorter days stay (6 days), and lower cost/case ($16,000)). This data suggests that patients with abrupt vessel closure or its proxy have significantly different clinical outcomes (mortality), and degrees of resource utilization (days stay, and cost).

Results Table 2:
Abrupt Vessel Closure Outcomes

| angioplasty | Mortality | days stay | cost | n |
|---|---|---|---|---|
| no cabg | 5% | 6 | $16,000 | 663 |
| Cabg | 13% | 16 | $72,000 | 24 |

Combining the information found in Results Table 1: Abrupt Vessel Closure By Stent Usage (patients with stent placement have fewer abrupt vessel closure events) and Results Table 2: Abrupt Vessel Closure Outcomes (patients without abrupt vessel closure have better outcomes); a user can hypothesize that patients with acute MI undergoing coronary angioplasty with a stent have better outcomes than those patients who do not use a stent. Research shows that this hypothesis is accurate.

Using the event creation GUI, variables representing events (event proxies) can be created from any variable contained in the analytic or staging data stores 124, 114 (e.g. laboratory results, procedures, diagnoses, bed transfers (ward to critical care), discharge dispositions, blood pressure measurements, heart rate readings). Once created, the variables may be added to the appropriate analytic data table for analysis using the event analysis GUI.

Example 3

The event creation GUI allows a user to create more complex events, such as those based on a variable(s) taking on a particular range of values for a specified length of time. For example, using GUI 2: Event Creation, CABG Following Angioplasty the user may create an event that summarizes the occurance of an event with many episodes during the course of a hospitalization, such as tachycardia (an abnormally high heart rate). In Example 3, Analytic Data Table 7: Critical Care Detail, contains very detailed physiologic information from a patient's intensive care unit stay. Analytic Data Table 7: Critical Care Detail has, in part, the following variables:

Analytic Data Table 7:
Critical Care Detail (Variables)

| variable | storage type | display format | |
|---|---|---|---|
| ln | str8 | %9s | patient id |
| date | int | %d | |
| time | str5 | %9s | |
| hr | int | %8.0g | heart rate |
| bpsys | int | %8.0g | systolic blood pressure |
| bpdia | int | %8.0g | diastolic blood pressure |
| respiratoryrate | int | %8.0g | |

Analytic Data Table 7: Critical Care Detail (Observations)

| ln | date | time | hr | bpsys | bpdia | respiratory rate |
|---|---|---|---|---|---|---|
| 88888888 | Dec. 31, 1998 | 22:40 | 108 | | | 16 |
| 88888888 | Dec. 31, 1998 | 22:42 | 108 | 139 | 74 | 36 |
| 88888888 | Dec. 31, 1998 | 22:45 | 107 | | | 18 |
| 88888888 | Dec. 31, 1998 | 22:49 | 107 | | | 17 |
| 88888888 | Dec. 31, 1998 | 22:51 | 106 | | | 24 |
| 88888888 | Dec. 31, 1998 | 22:58 | 108 | | | 31 |
| 88888888 | Dec. 31, 1998 | 22:59 | 106 | | | 30 |
| 88888888 | Dec. 31, 1998 | 23:00 | 106 | | | 27 |
| 88888888 | Dec. 31, 1998 | 23:10 | 109 | | | 29 |
| 88888888 | Dec. 31, 1998 | 23:20 | 108 | | | 33 |
| 88888888 | Dec. 31, 1998 | 23:30 | 113 | | | 33 |
| 88888888 | Dec. 31, 1998 | 23:50 | 110 | | | 27 |
| 88888888 | Dec. 31, 1998 | 23:60 | 105 | | | 29 |
| 88888888 | Dec. 31, 1998 | 23:70 | 108 | | | 26 |
| 88888888 | Dec. 31, 1998 | 23:80 | 105 | | | 25 |
| 88888888 | Dec. 31, 1998 | 23:90 | 102 | | | 31 |
| 88888888 | Dec. 31, 1998 | 23:13 | 101 | | | 26 |
| 88888888 | Dec. 31, 1998 | 23:14 | 101 | 125 | 61 | 28 |
| 88888888 | Dec. 31, 1998 | 23:25 | 108 | | | 25 |
| 88888888 | Dec. 31, 1998 | 23:26 | 103 | | | 28 |
| 88888888 | Dec. 31, 1998 | 23:27 | 105 | | | 27 |
| 88888888 | Dec. 31, 1998 | 23:28 | 98 | | | 28 |
| 88888888 | Dec. 31, 1998 | 23:29 | 100 | | | 25 |
| 88888888 | Dec. 31, 1998 | 23:30 | 97 | | | 24 |
| 88888888 | Dec. 31, 1998 | 23:31 | 98 | | | 24 |

-continued

| | | Analytic Data Table 7: Critical Care Detail (Observations) | | | | |
|---|---|---|---|---|---|---|
| ln | date | time | hr | bpsys | bpdia | respiratory rate |
| 88888888 | Dec. 31, 1998 | 23:32 | 99 | | | 26 |
| 88888888 | Dec. 31, 1998 | 23:34 | 106 | | | 41 |
| 88888888 | Dec. 31, 1998 | 23:35 | 102 | | | 19 |
| 88888888 | Dec. 31, 1998 | 23:38 | 106 | | | 24 |
| 88888888 | Dec. 31, 1998 | 23:39 | 102 | | | 6 |
| 88888888 | Dec. 31, 1998 | 23:43 | 107 | | | 31 |
| 88888888 | Dec. 31, 1998 | 23:44 | 102 | | | 9 |
| 88888888 | Dec. 31, 1998 | 23:45 | 99 | | | 6 |
| 88888888 | Dec. 31, 1998 | 23:46 | 101 | | | 13 |
| 88888888 | Dec. 31, 1998 | 23:47 | 99 | | | 16 |
| 88888888 | Dec. 31, 1998 | 23:48 | 95 | | | 2 |
| 88888888 | Dec. 31, 1998 | 23:49 | 94 | | | 0 |
| 88888888 | Dec. 31, 1998 | 23:50 | 96 | | | 6 |
| 88888888 | Dec. 31, 1998 | 23:51 | 99 | | | 11 |
| 88888888 | Dec. 31, 1998 | 23:52 | 100 | | | 22 |

Similar information could be generated from any patient with a device that monitors and electronically records heart rate. To study an event composed of many episodes, the user would choose the value "all" in line 2.

| | |
|---|---|
| 1. | Analytic Data Table 1 = *icu_detail* |
| 2. | Episode = *all* (1=first, _N=last, default = all) |
| 3. | Event1 = *hr* |
| 4. | Event1 value = *>105* |
| 5. | Event1 duration = *>5* |
| 6. | Event2 = *none* |
| 7. | Event2 value = *none* |
| 8. | Event2 duration = *none* |
| 9. | Interval between event 1 and event 2 = *none* |
| 10. | Save results table = *tachycardia* |
| 11. | Analytic Data Table 2 = *none* |
| 12. | New analytic table = *none* |
| 13. | New variable name = *none* |

By choosing "episode=all" in line 2 of GUI 2: Event Creation, CABG Following Angioplasty, the first loop of Algorithm 18 (Part I) is used to produce the Interrogation Script 3: Tachycardia.

| Interrogation Script 3: Tachycardia |
|---|
| use analytic/*icudetail* |
|    gen event1=1 if *hr>105&hr~=.* |
| sort ln date time event1 |
|    quietly by ln:gen episode=1 if event1[_n-1]==.&event1==1 |
|    quietly by ln:gen epi_n=sum(episode) |
|    replace epi_n=. if event1==. |
| sort ln epi_n date time |
|    by ln epi_n:gen epi_time=(time[_N]-time[1]) if date[_N]==date[1] |
| compress |
|    egen epi_median=median(*hr*),by(ln epi_n) |
|    egen epi_max=max(*hr*),by(ln epi_n) |
|    egen epi_mean=mean(*hr*),by(ln epi_n) |
|    by ln epi_n:gen epi_time1=time[1] |
|    by ln epi_n:gen epi_timeN=time[_N] |
|    by ln epi_n:gen epi_date1=date[1] |
|    by ln epi_n:gen epi_dateN=date[_N] |
| sort ln epi_n |
|    quietly by ln epi_n:keep if _n==1 |
|    drop if epi_n==. |
|    drop if epi_time<5 |
|    drop if epi_time==. |
|    quietly by ln: gen n=_N |
|    egen time_total=sum(epi_time),by(ln) |

-continued

| Interrogation Script 3: Tachycardia |
|---|
| sort ln epi_time |
|    quietly by ln:keep if _n==_N |
|    keep epi* |
| save user/*tachycardia* |

The interrogation engine 116 uses Interrogation Script 3: Tachycardia to interrogate Analytic Data Table 7: Critical Care Detail and produces Analytic Data Table 8: Tachycardia, each observation represents an episode of tachycardia with an hr>105 and lasting at least five (5) minutes.

| | Analytic Data Table 8: Tachycardia | | | | | |
|---|---|---|---|---|---|---|
| ln | date | time | episode | median | max | mean |
| 88888888 | Dec. 31, 1998 | 22:40 | 1 | 108 | 113 | 108 |
| 88888888 | Jan. 1, 1999 | 1:13 | 7 | 111 | 113 | 111 |

The first observation (line) in Analytic Data Table 8: Tachycardia summarizes the first episode of tachycardia beginning on 31 December at 22:40 and ending at 23:50 encompassing the first 12 observations of Analytic Data Table 7: Critical Care Detail, observations; with a median heart rate of 108, and a maximum heart rate of 113. The second line summarizes the $7^{th}$ episode of tachycardia occurring on January 1 at 1:13 with a median heart rate of 111. Episodes 2: 6 are not summarized as they did not last at least 5 minutes. The user of the present invention again using the event creation GUI (GUI 2: Event Creation, CABG Following Angioplasty) can then interrogate the newly created Analytic Data Table to create a single tachycardia event, and make it available for analysis in the event analysis GUI (GUI 1: Event Analysis, CABG Following Angioplasty).

Report Formats

The present invention may allow a user working from the graphical user interface 126 to obtain and store results as charts, graphs, or tables 128. The results may then be easily exported to commercial software applications for inclusion in reports and presentations. The present invention may display the results as charts, tables, or graphs 128. Query parameters may also be displayed, saved, or exported with the results. Further, the present invention preferably provides for basic statistical analysis and data visualization (means, one-way and two-way tables, t-test, and 95% confidence limits) and means to visualize the data (line plots with 95% confidence limits, box and whiskers plots, histograms). In addition to traditional exporting, the user of the present invention can "copy" displayed results and graphics to a "clipboard," and then "paste" to a document in another application. The user may save results as flat files (ASCII or XML), or export to ASCII delimited/fixed files. In other words, the results may be displayed, formatted, or used in any standard manner by commonly available business intelligence application programs, graphic programs, word processing programs, or other display-type programs. These features provide the user of the present invention with great flexibility to add graphs, tables, or charts displaying analytic results to reports, presentations, or web pages.

FIGS. 7–17 show exemplary reports generated for Example 2. These reports are meant to be exemplary and are not meant to limit the scope of the invention.

Figure 7:
FIGS. 7–17 are exemplary reports that may be produced in conjunction with Example 2.
Figure 7:
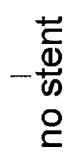
Figure 8:
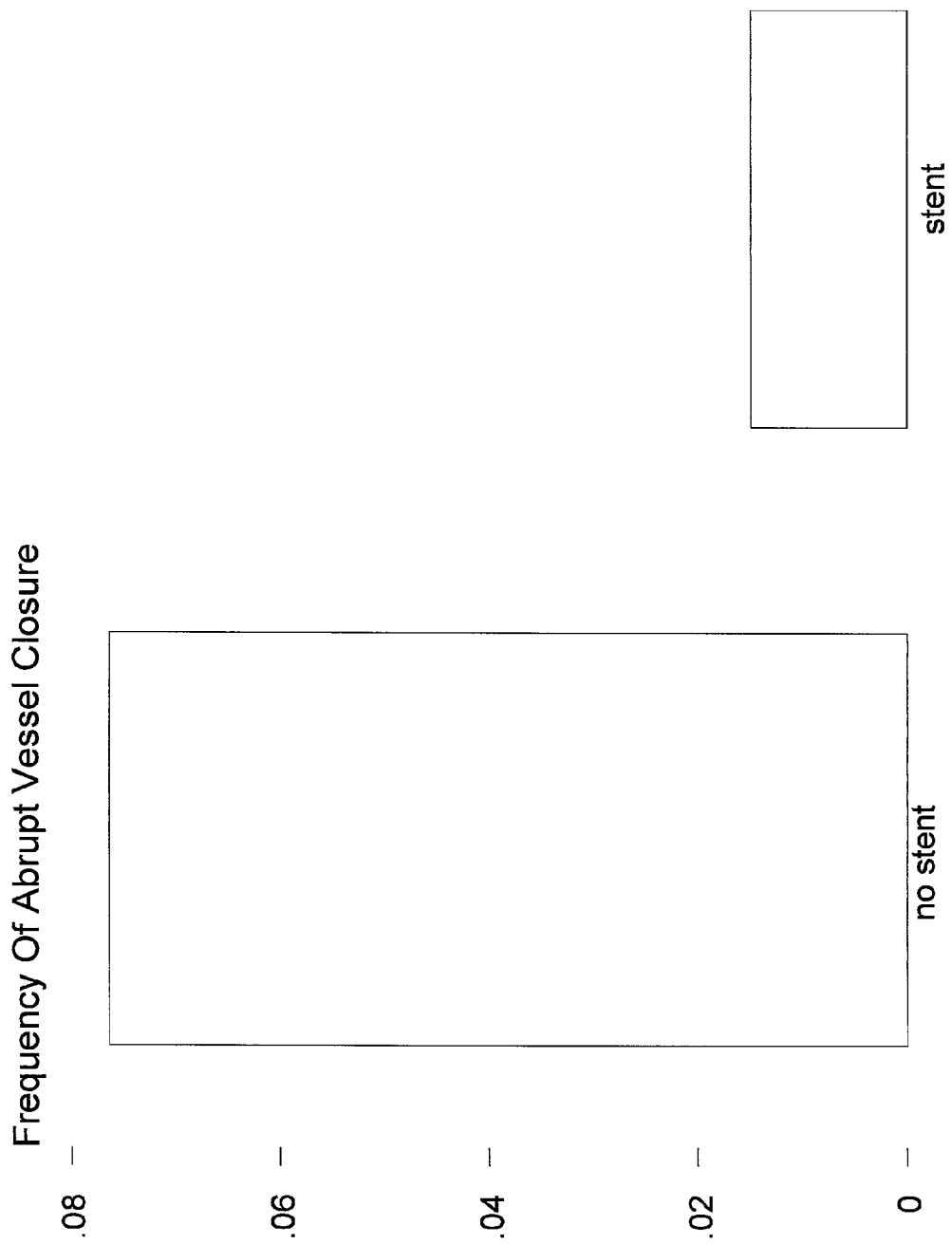
Figure 9:
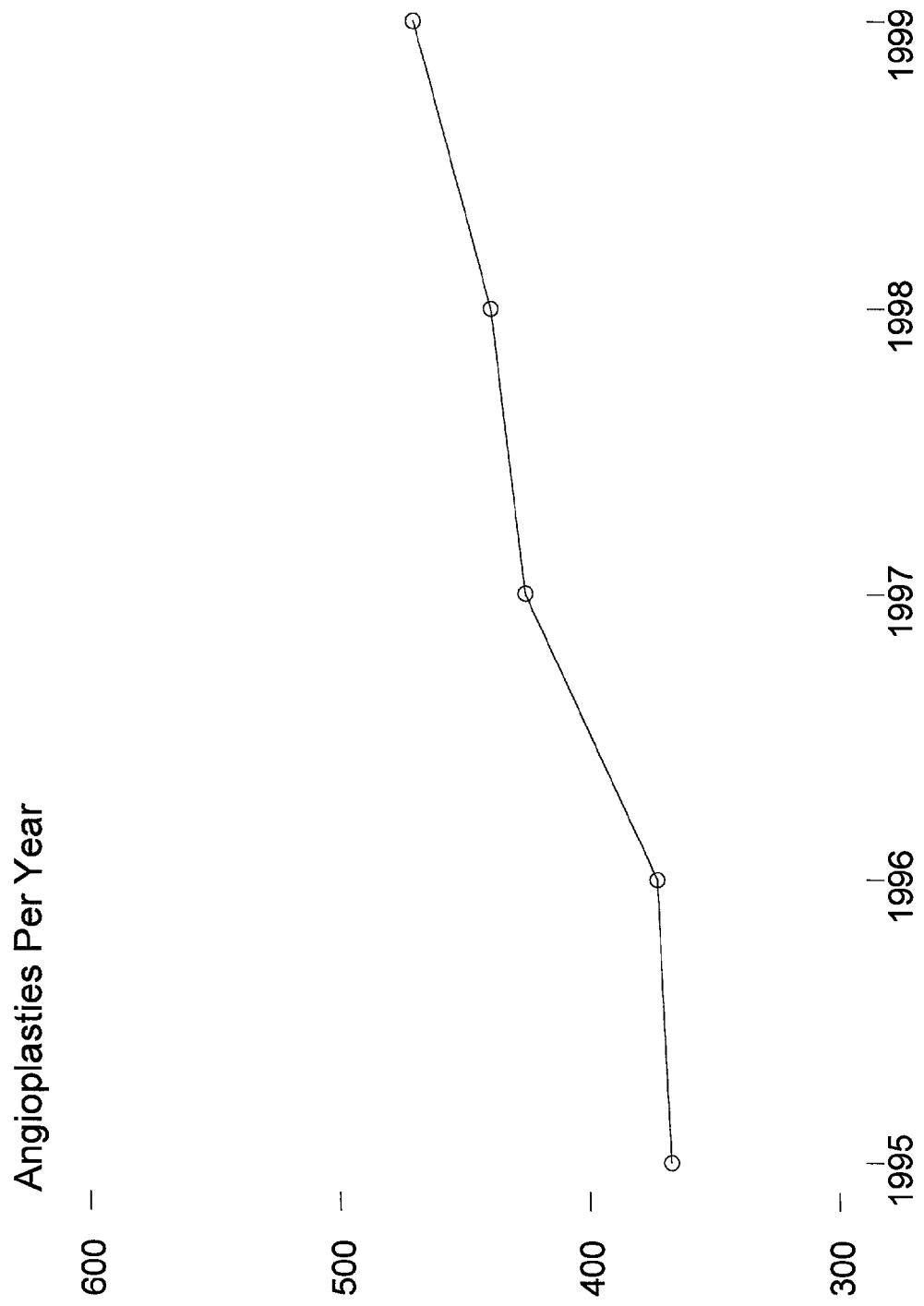
Figure 10:
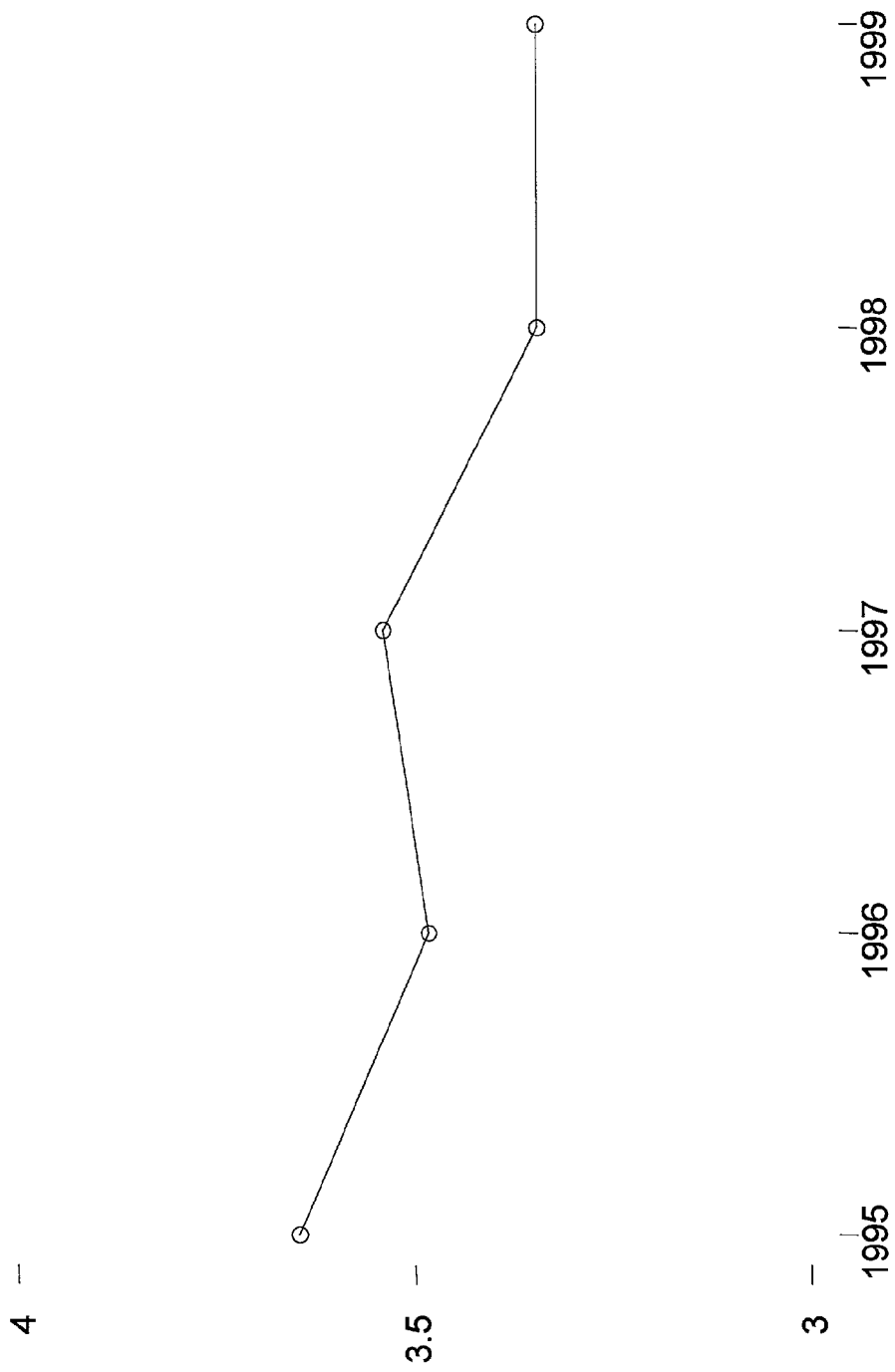
Figure 11:
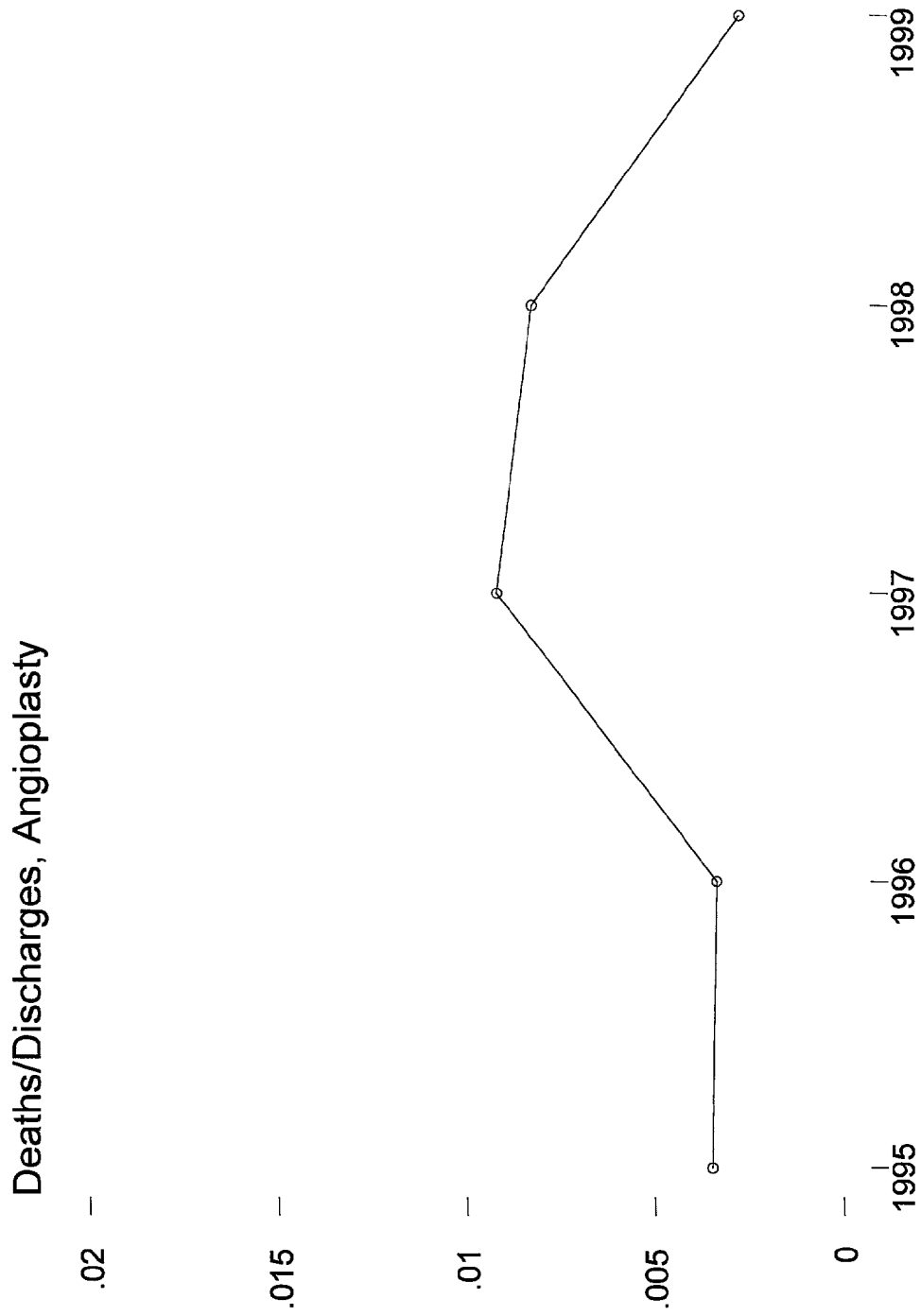
Figure 12:
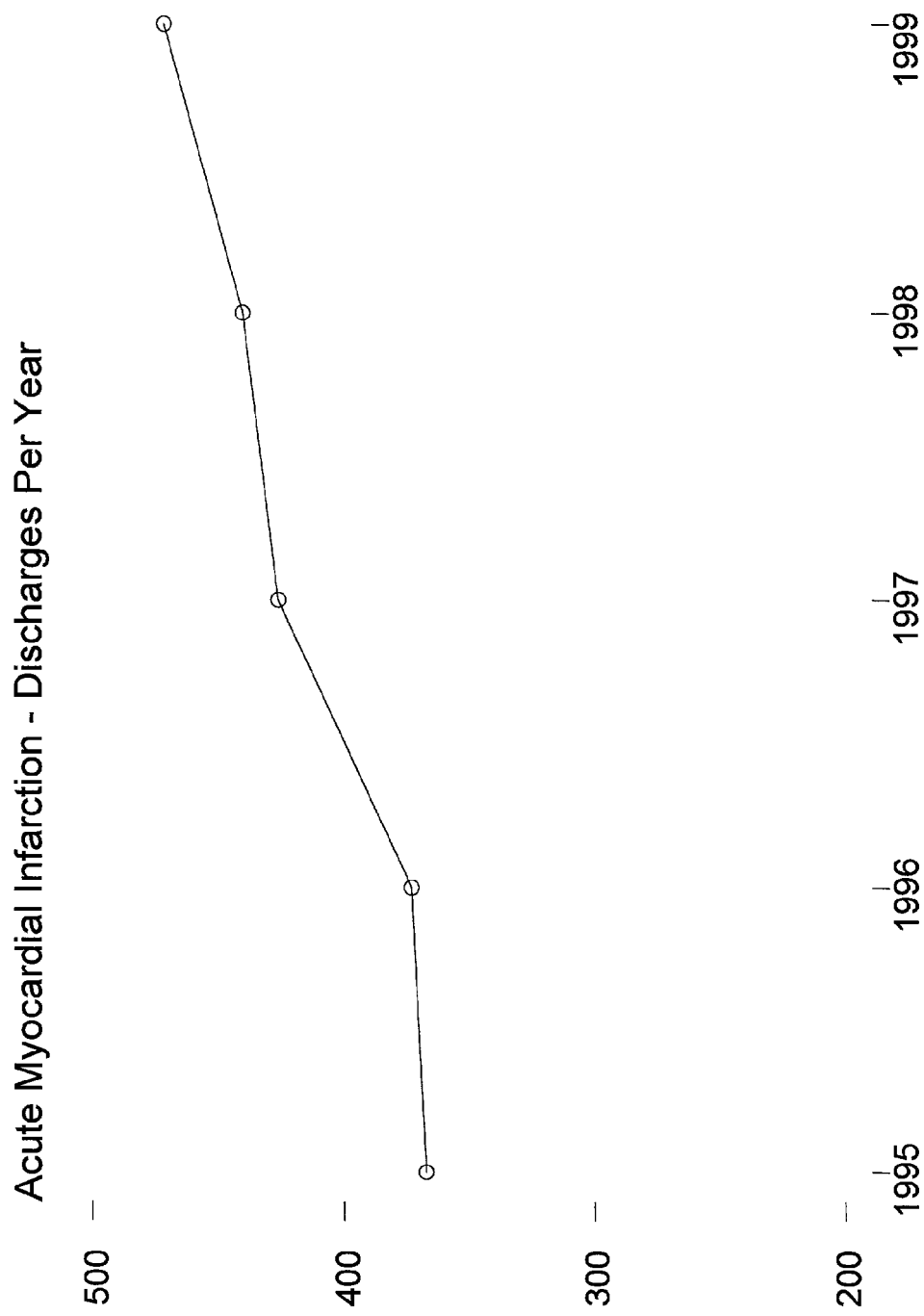
Figure 13:
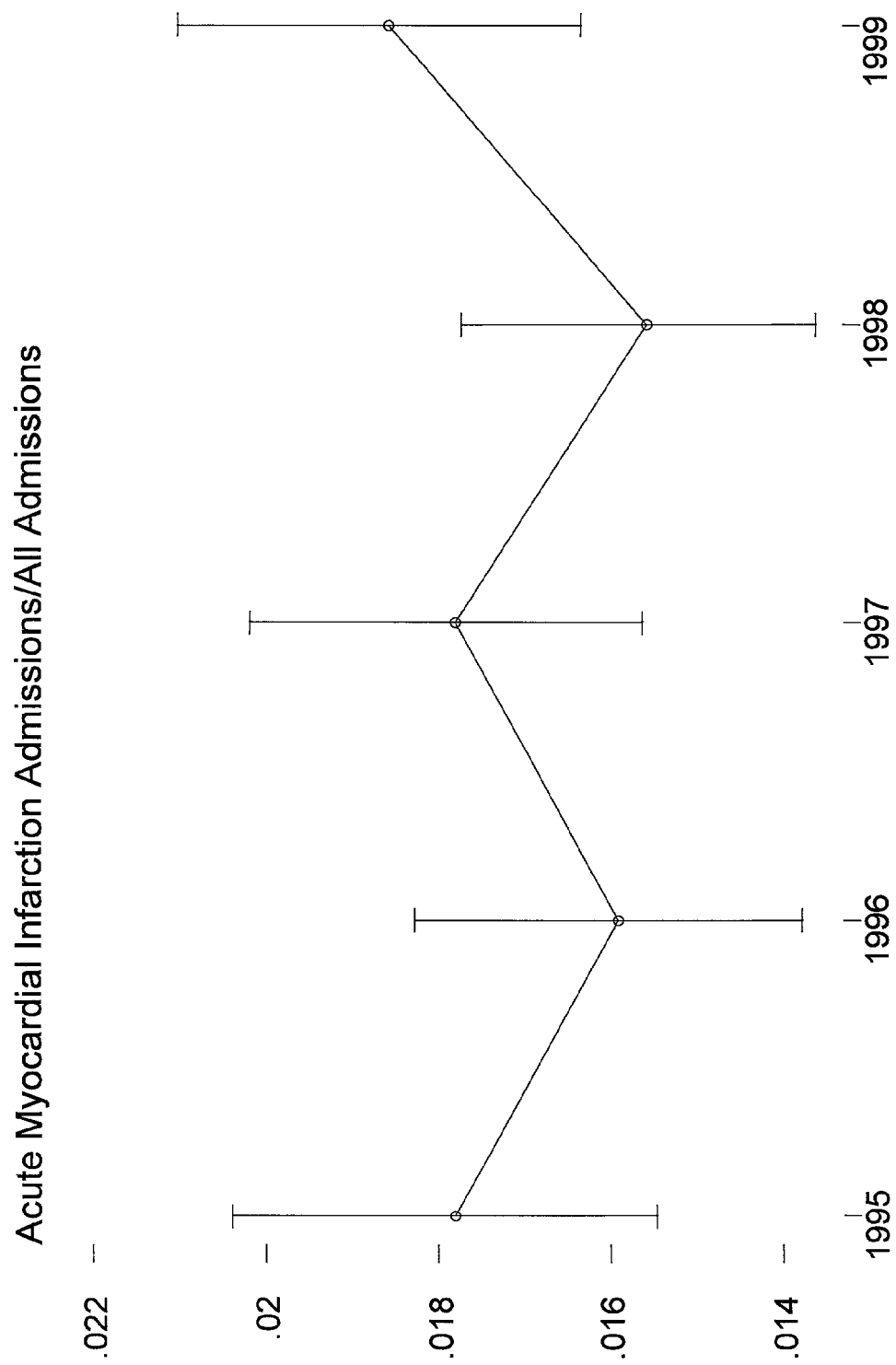
Figure 14:
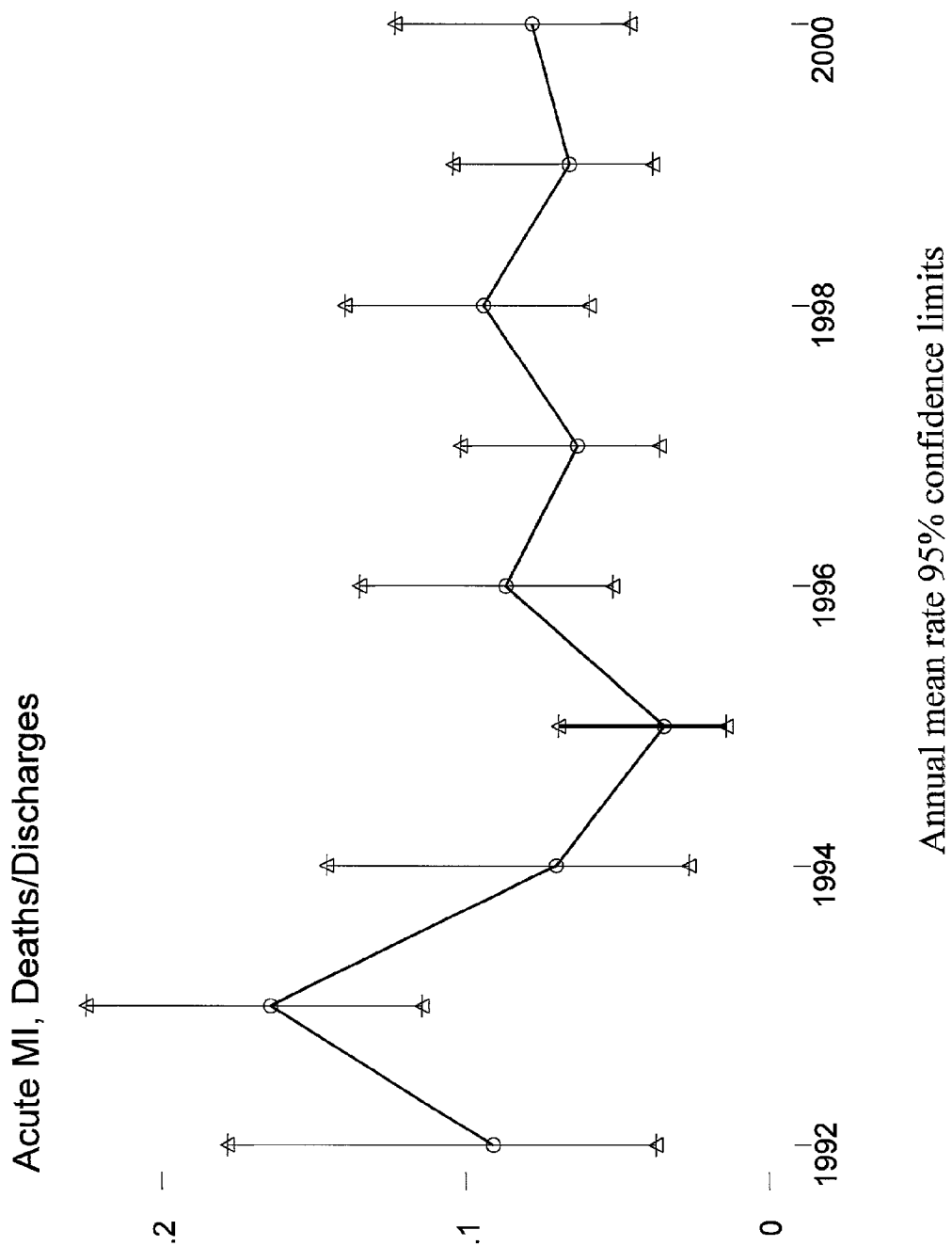
Figure 15:
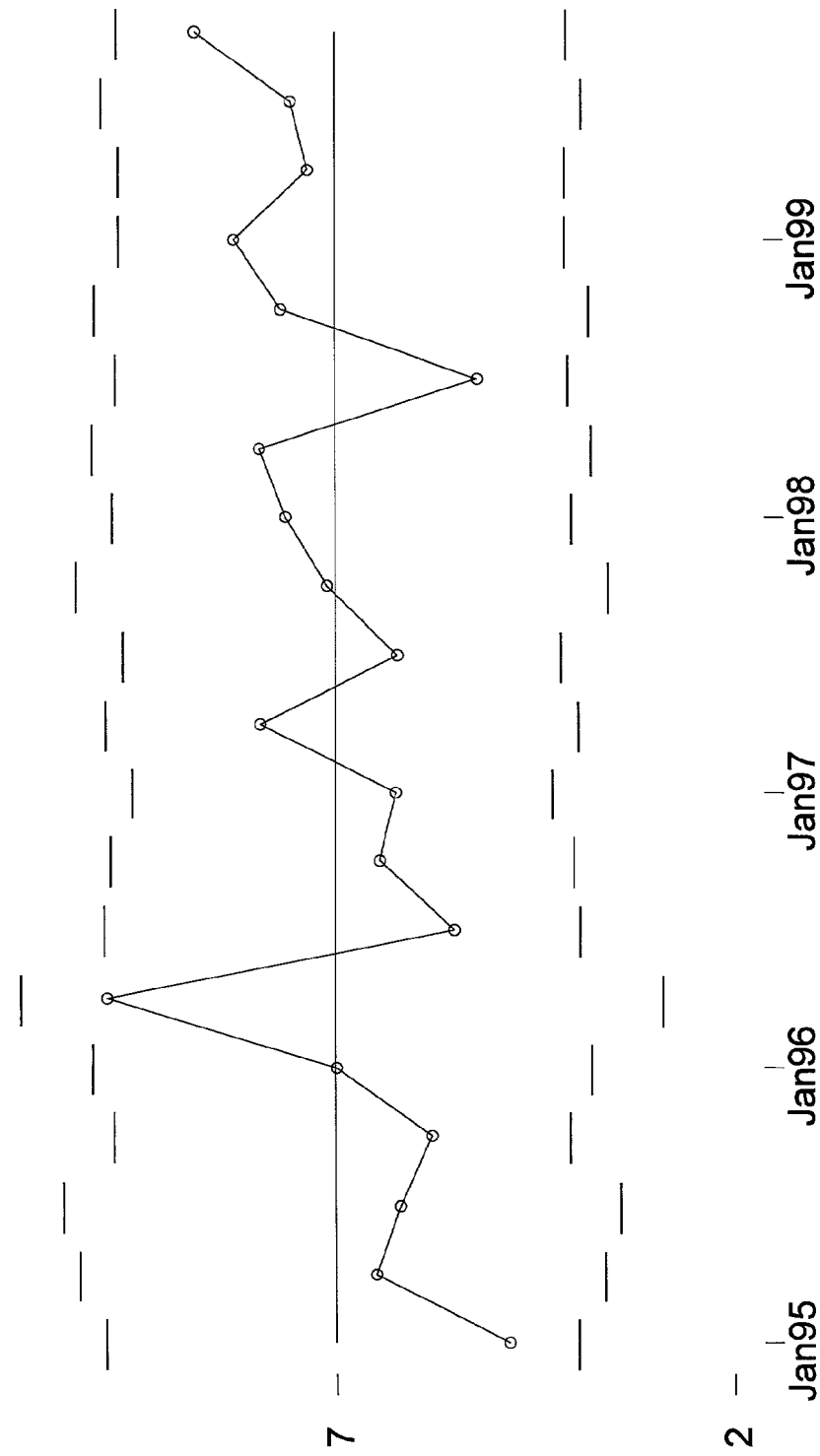
Figure 16:
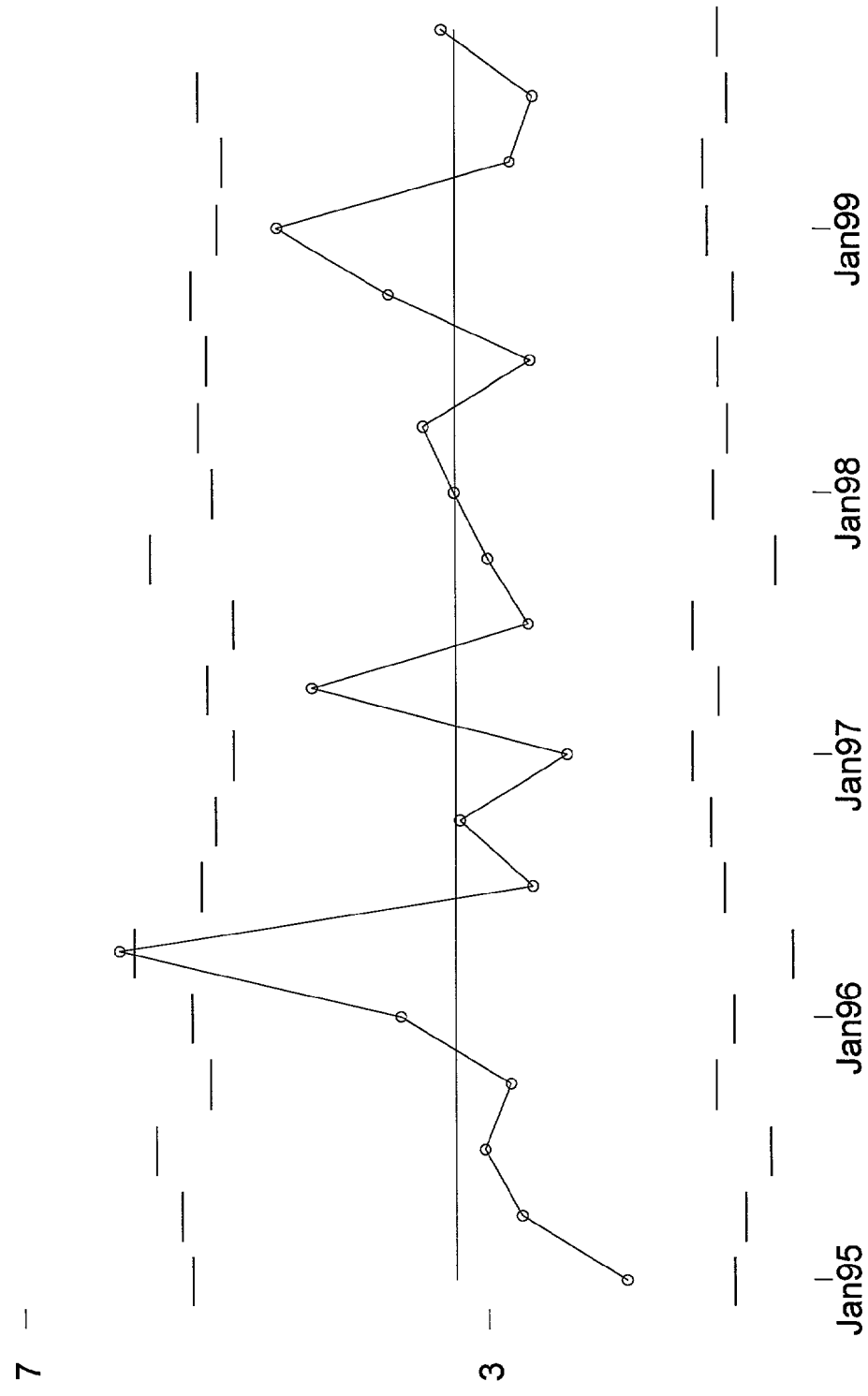

FIG. 7 is an example of a graphical output using the data in Results Table 1: Abrupt Vessel Closure By Stent Usage. As background, many hospitals monitor invasive cardiolgy procedures. Standard queries might include measures of: mortality, length of stay, critical care length of stay, cost, dye usage, second invasive procedure—same admission, acute myocardial infarction following an invasive cardiology procedure; and stratify these results by procedure type and performing cardiologist. Using the data created in GUI 1: Event Analysis, CABG Following Angioplasty, the fourth line of Interrogation Script 1: Abrupt Vessel Closure calls Algorithm 19: Report 95% Confidence Limits (catcibi). catcibi parses the values "stent" and "ccabg", and then executes as follows (in the following lines "stent" is parsed to '1', and "ccabg" to '2'):

---

Algorithm 19: Report 95% Confidence Limits (catcibi)

```
program drop_all
program define catcibi
sum '1'         /* '1' is group variable, eg stent*/
local i=_result(5)
tempvar xxx
quietly gen 'xxx'=_result(6)
while 'i'<='xxx' {
    quietly gen c'i'='2' if '1'=='i'   /*'2' is categorical
         variable, e.g. ccabg - coronary artery by-pass surgery
         following coronary angioplasty */
    quietly ci c'i',bi
    quietly upper c "'1'" 'i'
    local i='i'+1
}
sort '1'
quietly by '1':keep if _n==1
keep '1' cu cm cl
end
capture program define upper
    capture gen '1'm=.
    capture gen '1'u=.
    capture gen '1'l=.
    replace '1'u=$S_6 if'2'=='3'
    replace '1'm=$S_3 if'2'=='3'
    replace '1'l=$S_5 if'2'=='3'
end
```

---

The result would be the graph in FIG. 7 that shows mean rates with 95% confidence limits. The same data can be displayed in a bar chart such as that shown in FIG. 8. A choice of "table" instead of "graph" in GUI 1: Event Analysis, CABG Following Angioplasty, line 8 would produce Results Table 3: Abrupt Vessel Closure.

---

Results Table 3:
Abrupt Vessel Closure

|  | Rate | upper 95% CI | lower 95% CI |
|---|---|---|---|
| no stent | 0.076 | 0.133 | 0.039 |
| Stent | 0.015 | 0.034 | 0.005 |

---

The interrogation engine 116 employs standard statistical computation of mean and confidence limits provided in the STATA software application. The information contained in Results Table 3 can be displayed graphically in formats other than those found in FIG. 7 and FIG. 8. The user of the present invention can also export the results in a number of formats including, but not limited to a flat file format (e.g. Flat File Export 1: Abrupt Vessel Closure) and a XML format (e.g. XML Export 1: Abrupt Vessel Closure).

---

Flat File Export 1: Abrupt Vessel Closure

| stent | cm | cu | cl |
|---|---|---|---|
| 0 | .0763889 | .1325643 | .0387493 |
| 1 | .014881 | .0343846 | .0048492 |

XML Export 1: Abrupt Vessel Closure

```
{smcl}
{com}{sf}{ul off}{txt}{.-}
    log: {res}C:\projects\stj\2001\stent.smcl
{tt}log type: {res}smcl
{txt}opened on: {res}17 Nov 2001, 08:58:24
{txt}
{com}.li
{txt}          stent     cm        cu        cl
{txt} 1. {res}   0     .0763889   .1325643   .0387493
{txt} 2. {res}   1     .014881    .0343846   .0048492
{txt}
{com}.log close
{txt}log: {res}C:\projects\stj\2001\stent.smcl
{txt}log type: {res}smcl
{txt}closed on: {res}17 Nov 2001, 08:58:33
{txt}{.-}
{smcl}
{txt}{sf}{ul off}
```

---

Parameter Driven And Standard Reports/Queries

Reports can be "pushed out" over the Internet, or the user may conduct an ad hoc query either in a preformatted query or as an unformatted query. Reports that are pushed out, for example, may be sent by e-mail to a user or may be pushed out onto a Web site regularly accessed by the user. A user may, in fact, request specific monthly reports including cardiac quality of care, operative events, critical care, and inpatient mortality, as well as the more common resource utilization reports to be pushed out over e-mail two days after the end of each month. A preformatted query that a user conducts on an ad hoc basis may be conducted on a Web page that has pull-down menus (a parameter driven report). By choosing desired selections from one or more pull-down menus, the user could create a query. Referring to Example 2, utilization statistics may be obtained using Standard Report 1: Volume, Days Stay, Cost, Or Charge. Standard Report 1: Volume, Days Stay, Cost, Or Charge describes changes in patient volume, length of stay, and cost over time.

---

Standard Report 1:
Volume, Days Stay, Cost, Or Charge

```
use analytic/'1'    /* 1=name of analytic data table, i.e.
"hospital_encounter_table"*/
    keep if'2'='3'   /* 2=variable, e.g. angioplasty, 3=value of en,
"HOSP"*/
    sort year
        gen year_1=year[1]
        gen year_n=year[_N]
        gen month=month(eddate)
        gen time=month+12*month(year-year_1)
    sort time
        egen n=count(lid), by (time)
        egen mlos=mean(los),by(time)
        egen mcost=mean(cost),by(time)
    sort time
        quietly by time:keep if _n==2
        keep year time n mcost mlos
    outfile year
        graph n year,c(m) xlabel noax b2(" ") ylabel l1(angioplasty volume)
saving ('4')
    save using usr/'4'
```

Standard Report 1: Volume, Days Stay, Cost, Or Charge will create results in tabular form (Results Table 4: Angioplasty), graphically (see FIGS. 9–11), or export the data as an XML (XML Export 2: Angioplasty Statistics) or a flat file (Flat File Export 2: Angioplasty Statistics).

Results Table 4:
Angioplasty

| year | mortality | days stay | cost/case | number |
|------|-----------|-----------|-----------|--------|
| 1997 | .009%     | 3.54      | 9500      | 326    |
| 1998 | .008      | 3.35      | 9600      | 363    |
| 1999 | .003      | 3.35      | 8900      | 365    |

XML Export 2: Angioplasty Statistics

```
{smcl}
{com} {sf} {ul off} {txt} {.-}
    log: {res} C:\projects\stj\2001\stent.smcl
{txt}log type: {res}smcl
{txt}opened on: {res} 17 Nov 2001, 09:09:54
{txt}
{com}. table year if year>1996&year<2000,c(mean mort mean los mean cost count lid)
{txt}{hline 10} {c TT} {hline 47}
     year {c|} mean(mort) mean(los) mean(cost) N(lid)
{hline 10} {c +} {hline 47}
     1997 {c |} {res}.0187793   3.539906   13150.843   426
    {txt} 1998 {c |} {res}.0113636   3.345454   11380.395   440
    {txt} 1999 {c |} {res}.014862    3.346072   11616.068   471
{txt}{hline 10} {c BT} {hline 47}
{com}. log close
{txt}log: {res} C :\projects\stj\2001\stent.smcl
{txt}log type: {res}smcl
{txt}closed on: {res}17 Nov 2001, 09:09:59
{txt} {.-}
{smcl}
{txt} {sf} {ul off}
```

Flat File Export 2:
Angioplasty Statistics

| year | mort | los | cost  | n   |
|------|------|-----|-------|-----|
| 1997 | .019 | 3.5 | 13150 | 426 |
| 1998 | .011 | 3.3 | 11380 | 440 |
| 1999 | .015 | 3.3 | 11616 | 471 |

Figure 17:
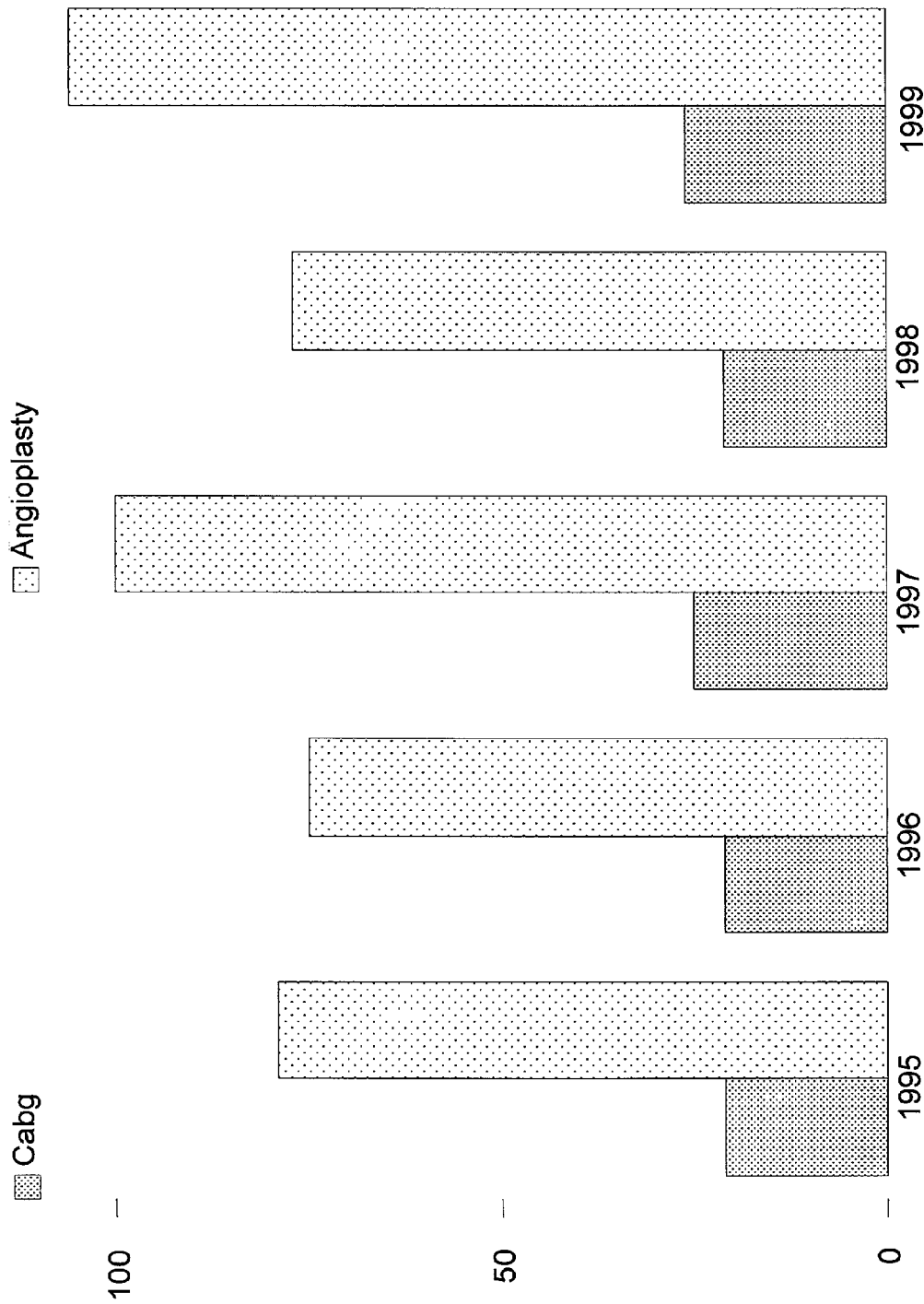

By substituting the value for acute MI "2" in Standard Report 1: Volume, Days Stay, Cost, Or Charge, the present invention could then for example generate the a line graph showing the number of acute MI patients discharged each year (FIG. 12), acute MI patients as a percentage of total discharges (FIG. 13); a graph representing the ratio of acute MI in-patient deaths each year with 95% confidence limits (FIG. 14); average length of hospital stay for acute MI patients each year in Statistical Process Control (SPC) format (FIG. 15); the average length of critical care unit stay for acute MI patients each year in SPC format (FIG. 16), or a bar graph showing the number of patients with an acute MI undergoing coronary artery by-pass surgery or coronary artery angiography (FIG. 17).

An unformatted query could be authored through a series of prompts or drop-down lists, or at the command line as a Boolean expression. Depending on the data available, an answer might or might not be available.

Libraries

The system has both public and user defined libraries. Initial implementation will include a public library of standard reports, events, stratifications, and queries available to all users. Users may store their own event, stratification, and query parameters for future use in a user defined library organized by the user in user defined directories and subdirectories. The public library may be augmented with user defined contributions after appropriate review and formatting.

Implementation

The present invention can be administered and updated as part of the administration of the underlying analytic or staging data stores 124, 114.

The environment recognizes different user levels: the major difference is the ability to use the independent ad hoc query capability. The basic-level user may rely on standard reports and pre-defined libraries of ad hoc queries. Training may consist of orientation to the interface, and the libraries. The more advanced (intermediate) user may be able to author independent queries, but probably will need additional training in their use. Super-user training requirements are similar to those of commercial statistics and data management applications like STATA® and SAS.

The present invention may be used with additional libraries of events, stratifications, views, and queries. In one preferred embodiment of the invention, these additional or updated libraries may be available as part of an annual maintenance contract. In an alternate preferred embodiment of the present invention, custom library development may be available. In yet another alternate preferred embodiment of the present invention, strategies may be developed for the analysis of data not currently available in the warehouse (e.g., output from the natural language processing of text reports). These strategies and data can then be incorporated into the analytic environment.

The present invention may be practiced using software license agreements. Alternatively, it may be practiced as an ASP and/or Internet delivery model (an "ASP/Internet delivery model") (FIGS. 3 and 4). The invention, however, is preferably platform-independent and can provide for a variety of methods of implementation: ASP, ASP while you build, incremental implementation, out-of-the-box, or a highly customized program.

One advantage of being implemented as an ASP/Internet delivery model is that it would provide access to new market segments previously unwilling or unable to invest in building and maintaining a healthcare data warehouse and analytics environment. Further, an ASP/Internet delivery model provides flexibility, avoids hardware/software dependency issues, and can easily be combined with a buy/build solution. Still further, an ASP/Internet delivery model allows broad customer access to the analytic results and infrastructure, bringing needed information to the consumer user level. The ASP/Internet delivery model also offers users a solution that they can use in a matter of months, rather than years, if they were to build it internally.

Certain users may be interested in an applications/analytic infrastructure to produce business insights (pure application provision) in which the user does not move data but does his own analysis. Other users may be interested in an e-portal to databased information in which the system hosts data/ structure data and provides some results, but the user is preferably able to access data over the Internet and can do his own analysis.

For healthcare providers, fiscal intermediaries, purchasers of healthcare, and providers of healthcare analytics, an ASP/Internet delivery model provides flexibility, avoids hardware/software-dependency issues, and can easily be combined with a buy/build solution. Specifically, the scalability of software of this invention allows healthcare organizations to incrementally implement functionality as they need it or as their budgets allow, and the platform independence of the technology allows the analytic solution to work with healthcare organizations' heterogeneous systems and existing data warehouses.

The ASP/Internet delivery model provides access to new market segments previously unwilling or unable to invest in building and maintaining a healthcare data warehouse and analytics environment. Individual consumers as well as smaller healthcare providers, fiscal intermediaries, purchasers of healthcare, and providers of healthcare analytics, for example, would benefit from this model. The ASP/Internet delivery model, therefore, allows broad customer access to the analytic results and infrastructure. Individual consumers and smaller organizations are able to get advanced enterprise and clinical analytics without the cost/risk of data warehousing and the requirements of maintaining their own data/analytic staffs. With the ASP/Internet delivery model, smaller customers may pay a fee for the functionality of the solution, rather than purchase and implement the software and hardware.

As shown in FIG. 4, using the ASP/Internet delivery model, the user, such as a healthcare provider, a fiscal intermediary, or a purchaser of healthcare, downloads data to a server where the analytic processing takes place. Users will then access the functionality of the solution with a PC and Internet browser via the Internet or a virtual private network. Smaller users may access the functionality of the solution without downloading data. As mentioned above, information may be pushed or pulled depending on the system capabilities and the user's access.

The implementation phase preferably includes data management professionals to map the data, validate the analytic algorithms, and automate the data migration process. In its preferred embodiment, the operational phase requires a data center, broadband Internet communications infrastructure, and application software.

Miscellaneous and Broadening

Although this invention has been primarily defined in terms of healthcare, it could easily be extended to other service industries, such as dental care, automobile service and maintenance, automobile defects, insurance, and financial markets.

The present invention is preferably hardware and software platform-independent, connecting to any ODBC-compliant data store. The system operates in UNIX or Windows and requires a database application (e.g., ORACLE®, SQL server) and, if internet based, an application server environment. One preferred embodiment may be written to run in STATA® (a statistics/data management application) but can be translated to other statistical/analytic/data mining or business intelligence applications (e.g., MineSet™, Business Objects®, COGNOS®, etc.) or fully programmed in C+ or PERL.

All user activity can be logged, edited, saved, and stored in user-defined libraries. User-defined stratifications, events, or queries may be saved in a user-specific library and later added to the system library by the system administrator or database administrator.

The terms and expressions employed in the foregoing specification are used therein as terms of description and not of limitation, and there is no intention in the use of such terms and expressions of excluding equivalents of the features shown and described or portions thereof, it being recognized that the scope of the invention is defined and limited only by the claims that follow.

What is claimed is:

1. An analytics and data warehousing infrastructure and services system, said system comprising:
   a. at least one source data store;
   b. at least one extractor for extracting source data from said source data store;
   c. at least one staging data store having at least one staging data table, said at least one staging data table being populated with said source data;
   d. at least one analytic data store for storing transformed data;
   e. at least one interrogation engine for moving and transforming data from said staging data table into said at least one analytic data store, said interrogation engine providing at least a partial denormalization of said data;
   f. said at least one interrogation engine for supporting ad hoc analysis and data mining from a user interface, said at least one interrogation engine facilitating user independent definition and user generation of user defined query concepts, said interrogation engine generating computer programming to modify and query said at least one analytic data store or said at least one staging data store, said user defined query concepts being user independently defined and user independently generated analytic concepts, stratifications, or events created from variables in said at least one analytic data store or said at least one staging data store; and
   g. at least one analytic and report means for generating analysis and reports;
   h. wherein said system uses an analytic data model that allows said user to extract useful information from said at least one analytic data store or said at least one staging data store, find patterns in said at least one analytic data store or said at least one staging data store and interpret patterns in said at least one analytic data store or said at least one staging data store.

2. The system of claim 1, wherein said interrogation engine includes at least one interrogation means for moving and transforming data, said interrogation means selected from the group consisting of:
   a. transformation algorithms;
   b. means for creating derived variables;
   c. means for restructuring data;
   d. analytic store update algorithms; and
   e. creation of derived variables algorithm.

3. The system of claim 1, wherein said interrogation engine allows independent authoring of new user defined query concepts to said at least one analytic data store or said at least one staging data store.

4. The system of claim 1, wherein said interrogation engine permits clinical user defined query concept questions of said at least one analytic data store or said at least one staging data store without knowing the question in advance.

5. The system of claim 1, wherein said said interrogation engine permits independent authoring of user defined query concepts that have not been pre-defined to said at least one analytic data store or said at least one staging data store.

6. The system of claim 1 wherein said at least one analytic and report means uses algorithms based on data mining and knowledge discovery.

7. The system of claim 1 wherein said system provides business solutions.

8. The system of claim 1 wherein said system is an application service provider model.

9. An analytics and data warehousing infrastructure and services system, said system comprising:
   a. at least one source data store;
   b. at least one extractor for extracting source data from said source data store;
   c. at least one staging data table, said at least one staging data table being populated with said source data;
   d. at least one analytic data store for storing transformed data;
   e. at least one interrogation engine for moving and transforming data from said staging data table into said at least one analytic data store, said interrogation engine providing at least a partial denormalization of said data;
   f. said at least one interrogation engine for supporting ad hoc analysis and data mining from a user interface, said at least one interrogation engine facilitating user independent definition and user generation of user defined query concepts, said interrogation engine generating computer programming to modify and query said at least one analytic data store or said at least one staging data store, said user defined query concepts being user independently defined and user independently generated analytic concepts, stratifications, or events created from variables in said at least one analytic data store or said at least one staging data store; and
   g. at least one analytic and report means for generating analysis and reports;
   h. wherein said system uses a data model based on a clinical rather than a financial understanding of healthcare.

10. An analytics and data warehousing infrastructure and services method, said method comprising:
   a. providing at least one source data store;
   b. extracting source data from said source data store;
   c. populating at least one staging data table with said source data;
   d. moving and transforming data from said staging data table into at least one analytic data store using at least one interrogation engine;
   e. supporting ad hoc analysis and data mining from a user interface of said at least one interrogation engine, said at least one interrogation engine facilitating user independent definition and user generation of user defined query concepts, said interrogation engine generating computer programming to modify and query said at least one analytic data store or said at least one staging data store, said user defined query concepts being user independently defined and user independently generated analytic concepts, stratifications, or events created from variables in said at least one analytic data store or said at least one staging data store; and
   f. generating analysis and reports using said at least one interrogation engine.

11. The method of claim 10 wherein said step of moving and transforming data from said staging data table into said at least one analytic data store further comprises the step of providing at least a partial denormalization of said data.

12. The method of claim 10, wherein said step of moving and transforming data from said staging data table into said at least one analytic data store further comprises at least one step selected from the group consisting of:
   a. performing transformation algorithms;
   b. creating derived variables;
   c. restructuring data;
   d. updating analytic stores; and
   e. creating derived variables algorithm.

13. The method of claim 10, wherein said step of supporting ad hoc analysis and data mining from a user interface of said at least one interrogation engine further comprises the step of independently authoring of new user defined query concepts to said at least one analytic data store or said at least one staging data store.

14. The method of claim 10, wherein said step of supporting ad hoc analysis and data mining from a user interface of said at least one interrogation engine further comprises the step of permitting clinical user defined query concepts of said at least one analytic data store or said at least one staging data store without knowing the question in advance.

15. The method of claim 10, wherein said step of supporting ad hoc analysis and data mining from a user interface of said at least one interrogation engine further comprises the step of permitting independent authoring of user defined query concepts that have not been pre-defined to said at least one analytic data store or said at least one staging data store.

16. An analytic and data warehousing infrastructure and services system, said system comprising:
   a. at least one extracted source data store;
   b. at least one staging data store having at least one stating data table;
   c. at least one analytic data store for storing transformed data;
   d. at least one staging data table loading algorithm for populating said at least one stating data table with source data;
   e. at least one data transformation algorithm for moving and transforming data from said at least one staging data table into said at least one analytic data store; and
   f. at least one query algorithm that facilitates user generation of user defined query concepts and generates said user defined query concepts computer programming to modify and query said at least one analytic data store or said at least one stating data store, said at least one query algorithm implemented by at least one interrogation engine;
   wherein said at least one query algorithm facilitates independent authoring of ad hoc queries that have not been pre-defined to said at least one analytic data store or said at least one staging data store.

17. The system of claim 16, wherein said at least one staging data table loading algorithm and said at least one data transformation algorithm are performed by said at least one interrogation engine.

18. The system of claim 16, wherein said at least one query algorithm facilitates independent authoring of new user defined query concepts to said at least one analytic data store or said at least one staging data store.

19. The system of claim 16, wherein said at least one query algorithm allows for clinical questions of said at least one at least one analytic data store or said at least one staging data store without knowing the question in advance.

20. The system of claim 1, wherein said interrogation engine includes means for creating derived variables.

21. The system of claim 9, wherein said interrogation engine includes means for creating derived variables.

22. The method of claim 10, wherein said step of moving and transforming data from said staging data table into said at least one analytic data store further comprises the step of creating derived variables.

23. The system of claim 16, wherein said at least one staging data table loading algorithm and said at least one data transformation algorithm create derived variables.

24. The system of claim 1, wherein said interrogation engine provides at least a partial denormalization of said data using an "entity—attribute—value (EAV)" schema.

25. The system of claim 9, wherein said interrogation engine provides at least a partial denormalization of said data using an "entity—attribute—value (EAV)" schema.

26. The method of claim 10, wherein said step of moving and transforming data further comprises the step of moving and transforming data from said staging data table into at least one analytic data store using an "entity—attribute—value (EAV)" schema.

27. The system of claim 16, wherein said at least one data transformation algorithm further comprises at least one data transformation algorithm for moving and transforming data from said at least one staging data table into said at least one analytic data store using an "entity—attribute—value (EAV)" schema.

28. The system of claim 1, wherein said interrogation engine facilitates user searching of said at least one analytic data store or said at least one staging data store for variables to use in stratification or event creation.

29. The system of claim 9, wherein said interrogation engine facilitates user searching of said at least one analytic data store or said at least one staging data store for variables to use in stratification or event creation.

30. The method of claim 10, further comprising the step of supporting user searching of said at least one analytic data store or said at least one staging data store for variables to use in stratification or event creation using said interrogation engine.

31. The system of claim 16, wherein said interrogation engine facilitates user searching of said at least one analytic data store or said at least one staging data store for variables to use in stratification or event creation.

* * * * *